(12) United States Patent
Jackson et al.

(10) Patent No.: US 11,623,067 B2
(45) Date of Patent: *Apr. 11, 2023

(54) CATHETER

(71) Applicant: Covidien LP, Mansfield, MA (US)

(72) Inventors: Brad Jackson, San Diego, CA (US); Rick Williams, Laguna Niguel, CA (US); John Nguyen, Laguna Beach, CA (US); Anthony Huynh, Wildomar, CA (US)

(73) Assignee: COVIDIEN LP, Mansfield, MA (US)

( * ) Notice: Subject to any disclaimer, the term of this patent is extended or adjusted under 35 U.S.C. 154(b) by 784 days.

This patent is subject to a terminal disclaimer.

(21) Appl. No.: 16/454,524

(22) Filed: Jun. 27, 2019

(65) Prior Publication Data
US 2019/0314604 A1    Oct. 17, 2019

Related U.S. Application Data

(63) Continuation of application No. 14/725,108, filed on May 29, 2015, now Pat. No. 10,357,631.

(51) Int. Cl.
A61M 25/00    (2006.01)
B29C 53/00    (2006.01)
(Continued)

(52) U.S. Cl.
CPC .... *A61M 25/0053* (2013.01); *A61M 25/0012* (2013.01); *A61M 25/0045* (2013.01);
(Continued)

(58) Field of Classification Search
CPC .......... A61M 25/0012; A61M 25/0045; A61M 25/0053; A61M 25/0054; A61M 25/10; A61M 2025/0059; A61B 2017/22079

See application file for complete search history.

(56) References Cited

U.S. PATENT DOCUMENTS 4,354,491 A    10/1982    Marbry
4,405,314 A     9/1983    Cope
(Continued)

FOREIGN PATENT DOCUMENTS

CN    1382499 A       12/2002
CN    103635224 A      3/2014
(Continued)

OTHER PUBLICATIONS

Response to the Examination Report from counterpart Canadian Application No. 2,987,819, dated Jun. 4, 2020, 32 pp.
(Continued)

*Primary Examiner* — Laura A Bouchelle
*Assistant Examiner* — John A Doubrava
(74) *Attorney, Agent, or Firm* — Shumaker & Sieffert, P.A.

(57) ABSTRACT

In some examples, a catheter comprises an inner liner, an outer jacket, and a structural support member positioned between at least a portion of the inner liner and the outer jacket. The inner liner, the outer jacket, and the structural support member define a catheter body that comprises a proximal portion having a first outer diameter, a distal portion having a second outer diameter less than the first outer diameter, the distal portion including a distal end of the catheter body, and a medial portion positioned between the proximal portion and the distal portion, the medial portion tapering from the first outer diameter to the second outer diameter.

23 Claims, 5 Drawing Sheets

US 11,623,067 B2

Page 2

(51) Int. Cl.
*B29C 63/00* (2006.01)
*A61B 17/22* (2006.01)
*A61M 25/09* (2006.01)
*B29K 75/00* (2006.01)
*B29L 31/00* (2006.01)
*B29K 27/18* (2006.01)
*B29C 63/42* (2006.01)

(52) U.S. Cl.
CPC .............. *B29C 53/00* (2013.01); *B29C 63/00* (2013.01); *A61B 2017/22079* (2013.01); *A61M 25/09* (2013.01); *A61M 2025/0042* (2013.01); *A61M 2025/0046* (2013.01); *A61M 2025/0057* (2013.01); *A61M 2025/0059* (2013.01); *A61M 2210/0687* (2013.01); *A61M 2210/12* (2013.01); *B29C 63/42* (2013.01); *B29K 2027/18* (2013.01); *B29K 2075/00* (2013.01); *B29L 2031/7542* (2013.01)

(56) References Cited

U.S. PATENT DOCUMENTS

| | | | |
|---|---|---|---|
| 4,425,919 A | | 1/1984 | Alston, Jr. et al. |
| 4,676,229 A | * | 6/1987 | Krasnicki .............. A61B 1/042 |
| | | | 600/153 |
| 4,739,768 A | | 4/1988 | Engelson |
| 4,763,671 A | | 8/1988 | Goffinet |
| 4,930,521 A | | 6/1990 | Metzger et al. |
| 4,976,690 A | | 12/1990 | Solar et al. |
| 5,007,901 A | | 4/1991 | Shields |
| 5,217,482 A | | 6/1993 | Keith |
| 5,308,342 A | | 5/1994 | Sepetka et al. |
| 5,358,493 A | | 10/1994 | Schweich et al. |
| 5,380,304 A | | 1/1995 | Parker |
| 5,380,307 A | | 1/1995 | Chee et al. |
| 5,405,338 A | | 4/1995 | Kranys |
| 5,423,776 A | | 6/1995 | Haindl |
| 5,437,632 A | | 8/1995 | Engelson |
| 5,499,973 A | | 3/1996 | Saab |
| 5,531,685 A | | 7/1996 | Hemmer et al. |
| 5,649,909 A | | 7/1997 | Cornelius |
| 5,695,483 A | | 12/1997 | Samson |
| 5,702,373 A | | 12/1997 | Samson |
| 5,755,704 A | | 5/1998 | Lunn |
| 5,792,124 A | | 8/1998 | Horrigan et al. |
| 5,830,227 A | | 11/1998 | Fischell et al. |
| 5,833,604 A | | 11/1998 | Houser et al. |
| 5,951,495 A | | 9/1999 | Berg et al. |
| 5,954,651 A | * | 9/1999 | Berg .................. A61M 25/005 |
| | | | 600/585 |
| 5,957,893 A | | 9/1999 | Luther et al. |
| 5,971,975 A | | 10/1999 | Mills et al. |
| 5,984,907 A | | 11/1999 | McGee et al. |
| 6,045,547 A | | 4/2000 | Ren et al. |
| 6,143,013 A | | 11/2000 | Samson et al. |
| 6,213,995 B1 | * | 4/2001 | Steen .................. A61B 18/14 |
| | | | 604/527 |
| 6,217,565 B1 | | 4/2001 | Cohen |
| 6,319,244 B2 | | 11/2001 | Suresh et al. |
| 6,436,112 B2 | | 8/2002 | Wensel et al. |
| 6,524,302 B2 | | 2/2003 | Kelley |
| 6,582,536 B2 | | 6/2003 | Shimada |
| 6,591,472 B1 | | 7/2003 | Noone et al. |
| 6,841,214 B1 | | 1/2005 | Keith et al. |
| 7,306,585 B2 | | 12/2007 | Ross |
| 7,527,606 B2 | | 5/2009 | Oepen |
| 7,625,337 B2 | | 12/2009 | Campbell et al. |
| 7,658,723 B2 | | 2/2010 | Von Oepen et al. |
| 8,034,045 B1 | | 10/2011 | Lyons |
| 8,105,246 B2 | | 1/2012 | Voeller et al. |
| 8,142,413 B2 | | 3/2012 | Root et al. |
| 8,241,245 B2 | | 8/2012 | Markel et al. |
| 8,251,976 B2 | | 8/2012 | Zhou |
| 8,282,677 B2 | | 10/2012 | O'Connor et al. |
| 8,323,432 B2 | | 12/2012 | Quint |
| 8,382,738 B2 | | 2/2013 | Simpson et al. |
| 8,574,283 B1 | | 11/2013 | Kamat |
| 8,608,754 B2 | | 12/2013 | Wensel et al. |
| 8,652,193 B2 | | 2/2014 | Dorn |
| 8,684,999 B2 | | 4/2014 | Tegg et al. |
| 8,702,679 B2 | | 4/2014 | Deckman et al. |
| 8,725,228 B2 | | 5/2014 | Koblish et al. |
| 8,758,295 B2 | | 6/2014 | Schaeffer |
| 8,911,424 B2 | | 12/2014 | Weadock et al. |
| 8,926,560 B2 | | 1/2015 | Dinh et al. |
| 9,023,011 B2 | | 5/2015 | Griffin et al. |
| 9,352,116 B2 | | 5/2016 | Guo et al. |
| 10,046,138 B2 | | 8/2018 | Faherty et al. |
| 10,357,631 B2 | * | 7/2019 | Jackson .................. B29C 63/00 |
| 10,398,874 B2 | | 9/2019 | Williams et al. |
| 2002/0156459 A1 | | 10/2002 | Ye et al. |
| 2003/0114831 A1 | * | 6/2003 | Wang .................. A61L 29/126 |
| | | | 604/525 |
| 2003/0135198 A1 | | 7/2003 | Berhow et al. |
| 2003/0145915 A1 | | 8/2003 | Shimada |
| 2004/0087933 A1 | | 5/2004 | Lee et al. |
| 2004/0153049 A1 | | 8/2004 | Hewitt et al. |
| 2004/0243102 A1 | | 12/2004 | Berg et al. |
| 2005/0115624 A1 | | 6/2005 | Walak |
| 2005/0131387 A1 | * | 6/2005 | Pursley .............. A61M 25/005 |
| | | | 604/524 |
| 2006/0030835 A1 | * | 2/2006 | Sherman .................. A61F 2/958 |
| | | | 604/526 |
| 2006/0264905 A1 | | 11/2006 | Eskridge et al. |
| 2008/0048011 A1 | | 2/2008 | Weller |
| 2009/0030400 A1 | * | 1/2009 | Bose .................. A61M 25/0023 |
| | | | 604/528 |
| 2009/0240235 A1 | * | 9/2009 | Murata .............. A61M 25/0012 |
| | | | 427/2.3 |
| 2010/0049167 A1 | | 2/2010 | Myers |
| 2010/0049192 A1 | | 2/2010 | Holtz et al. |
| 2011/0028940 A1 | | 2/2011 | Lorenz |
| 2011/0238041 A1 | | 9/2011 | Lim et al. |
| 2011/0245775 A1 | | 10/2011 | Tekulve |
| 2012/0041411 A1 | | 2/2012 | Horton et al. |
| 2012/0101480 A1 | | 4/2012 | Ingle et al. |
| 2012/0116350 A1 | | 5/2012 | Strauss et al. |
| 2012/0172717 A1 | | 7/2012 | Gonda |
| 2012/0245562 A1 | | 9/2012 | Bihlmaier |
| 2012/0303051 A1 | | 11/2012 | Matsuura |
| 2013/0090632 A1 | | 4/2013 | Tahara et al. |
| 2013/0172851 A1 | | 7/2013 | Shimada et al. |
| 2013/0245610 A1 | | 9/2013 | Haslinger et al. |
| 2013/0253417 A1 | | 9/2013 | Dinh et al. |
| 2014/0046297 A1 | | 2/2014 | Shimada et al. |
| 2014/0114290 A1 | | 4/2014 | Okamura |
| 2014/0155879 A1 | | 6/2014 | McRae et al. |
| 2014/0173878 A1 | | 6/2014 | Merk et al. |
| 2014/0243963 A1 | | 8/2014 | Sheps et al. |
| 2014/0277058 A1 | | 9/2014 | Wu |
| 2015/0038908 A1 | | 2/2015 | Antonucci |
| 2015/0100043 A1 | | 4/2015 | Govari et al. |
| 2015/0157827 A1 | | 7/2015 | Glasel |
| 2015/0216692 A1 | | 8/2015 | Shannon et al. |
| 2016/0346503 A1 | | 12/2016 | Jackson et al. |
| 2016/0346507 A1 | | 12/2016 | Jackson et al. |
| 2017/0252535 A1 | * | 9/2017 | Ganske .............. A61M 25/0041 |
| 2018/0296811 A1 | | 10/2018 | Chan et al. |
| 2019/0314604 A1 | | 10/2019 | Jackson et al. |
| 2020/0406006 A1 | | 12/2020 | Shimada et al. |

FOREIGN PATENT DOCUMENTS

| | | |
|---|---|---|
| CN | 104220014 A | 12/2014 |
| CN | 104337512 A | 2/2015 |
| EP | 0530970 A1 | 3/1993 |
| EP | 0643979 A1 | 8/1994 |
| EP | 0810003 A2 | 5/1997 |
| EP | 2213325 A1 | 8/2010 |
| EP | 2572749 A2 | 3/2013 |
| EP | 2979725 B1 | 9/2018 |
| JP | H09-501094 | 2/1997 |

(56) References Cited

FOREIGN PATENT DOCUMENTS

| | | |
|---|---|---|
| JP | 2006501969 A | 1/2006 |
| JP | 2007512914 A | 5/2007 |
| JP | 2008229160 A | 10/2008 |
| JP | 2011062354 A | 3/2011 |
| JP | 2012029872 | 2/2012 |
| JP | 2012187263 A | 10/2012 |
| JP | 2013066720 A | 4/2013 |
| JP | 5-192411 B2 | 5/2013 |
| JP | 2014520601 A | 8/2014 |
| JP | 2016174829 A | 10/2016 |
| WO | 9305842 A1 | 4/1993 |
| WO | 2004033015 A1 | 4/2004 |
| WO | 2009054509 A1 | 4/2009 |
| WO | 2010068793 A1 | 6/2010 |
| WO | 2013185148 A1 | 12/2013 |
| WO | 2014157164 A1 | 10/2014 |

OTHER PUBLICATIONS

Third Office Action from counterpart Canadian Application No. 2,987,819 dated Feb. 5, 2020, 3 pp.
Examination Report from counterpart Indian Application No. 201717040684, dated Oct. 26, 2020, 6 pp.
Second Office Action, and translation thereof, from counterpart Chinese Application No. 201680031340.8, dated Jun. 12, 2020, 24 pp.
Response to Australian Office Action dated Apr. 22, 2020, from counterpart Australian application No. 2019202569, filed Jul. 8, 2020, 16 pp.
Response to Indian Office Action dated Oct. 26, 2020, from counterpart Indian application No. 201717040684, filed Apr. 26, 2021, 14 pp.
"Biotechnology Companies; Patent Application Titled "Steerable Catheter Having Intermediate Stiffness Transition Zone" Published Online," Biotech Business Week, NewsRx LLC, Sep. 22, 2014, 5 pp.
"Entellus Medical, Inc.; Patent Issued for Guide Catheter and Method of Use," Medical Devices & Surgical Technology Week, NewsRx, Mar. 16, 2014, 6 pp.
"Thermoset Adhesives Information," Engineering 360, IEEE, accessed from http://www.globalspec.com/learnmore/materials_chemicals/adhesives/thermoset_adhesives on Aug. 7, 2017, 3 pp.
"Braided Catheter Shafts & Coiled Catheter Shafts," AdvancedCath, retrieved from http://advancedcathetermanufacturing.com/braided-and-coiled-catheter-shafts/ on Jan. 19, 2015, 2 pp.
"Braid-Reinforced Shafts," Vention Medical, retrieved from http://www.ventionmedical.com/products-and-services/braid-reinforced-shafts/ on Jan. 19, 2015, 2 pp.
"C-Flex™ Ureteral Catheters," Boston Scientific, retrieved from http://www.bostonscientific.com/en-US/products/catheters-ureteral/c-flex.html on Jan. 15, 2015, 3 pp.
Hartford, "New Extrusion Techniques Advance Catheter Design," Medical Device and Diagnostic Industry, Feb. 20, 2013, 4 pp.
"Marathon™ Flow Directed Micro Catheters," Covidien, retrieved from http://www.ev3.net/neuro/us/micro-catheters/marathontrade-flow-directed-catheter.htm on Jan. 19, 2015, 2 pp.
"Microcatheters: Valet® Microcatheter," Volcano Corporation, retrieved from http://www.volcanocorp.com/products/valet.php#.VddxLflVhvB on Jan. 15, 2015, 2 pp.
"Putnam Plastics New Taper—TIE™ Technology Optimizes Variable Flexibility of Medical Catheter Shafts," Dec. 18, 2012, 1 pp.
"SIDEKICK® Support Catheter, Enhanced CROSSER® Catheter Deliverability," Bard Peripheral Vascular, 2013, 2 pp. (Applicant points out, in accordance with MPEP 609.04(a), that the year of publication, 2013, is sufficiently earlier than the effective U.S. filing date, so that the particular month of publication is not in issue.).
Web page, Engineering 360, Definition of Thermoset Adhesive retrieved from http://www.globalspec.com/learnmore/materials_chemicals/adhesives/thermoset_adhesives, Aug. 7, 2017, 3 pp.
First Examination Report from counterpart Australian Application No. 2016271022, dated Jan. 16, 2018, 4 pp.
Response to First Examination Report from counterpart Australian Application No. 2016271022, dated Jan. 16, 2018, filed May 25, 2018, 25 pp.
Second Examination Report from counterpart Australian Application No. 2016271022, dated Jul. 5, 2018, 6 pp.
Response to Second Examination Report from counterpart Australian Application No. 2016271022, dated Jul. 5, 2018, filed Sep. 25, 2018, 3 pp.
Third Examination Report from counterpart Australian Application No. 2016271022, dated Nov. 16, 2018, 3 pp.
Response to Third Examination Report from counterpart Australian Application No. 2016271022, dated Nov. 16, 2018, filed Jan. 3, 2019, 20 pp.
Notice of Acceptance and Allowed Claims from counterpart Australian Application No. 2016271022, dated Jan. 11, 2019, 8 pp.
Examination Report from counterpart Canadian Application No. 2,987,819, dated Sep. 20, 2018, 4 pp.
Response to Examination Report from counterpart Canadian Application No. 2,987,819, dated Sep. 20, 2018, filed Mar. 20, 2019, 33 pp.
Examination Report from counterpart Canadian Application No. 2,987,819, dated Jun. 4, 2019, 3 pp.
Response to Examination Report from counterpart Canadian Application No. 2,987,819, dated Jun. 4, 2019, filed Dec. 2, 2019, 11 pp.
Communication pursuant to Rules 161(1) and 162 EPC from counterpart European Application No. 16727120.4, dated Jan. 12, 2018, 4 pp.
Response to Communication pursuant to Rules 161(1) and 162 EPC from counterpart European Application No. 16727120.4, dated Jan. 12, 2018, filed Jul. 12, 2018, 12 pp.
Notification of Reasons for Rejection, and translation thereof, from counterpart Japanese Application No. 2017-561874, dated Sep. 19, 2018, 26 pp.
Notice of Reasons for Rejection, and translation thereof, from counterpart Japanese Application No. 2017-561874, dated Mar. 18, 2019, 25 pp.
International Search Report and Written Opinion from counterpart International Application No. PCT/US2016/034281, dated Aug. 9, 2016, 11 pp.
Prosecution History from U.S. Appl. No. 14/725,108, dated Jun. 16, 2017 through May 28, 2019, 112 pp.
Prosecution History from U.S. Appl. No. 14/725,283, dated Sep. 7, 2017 through May 15, 2019, 101 pp.
Prosecution History from U.S. Appl. No. 14/725,174, dated Aug. 10, 2017 through Feb. 5, 2020, 184 pp.
Examination Report from counterpart Australian Application No. 2019202569 dated Apr. 22, 2020, 3 pp.
Response to Office Action dated Feb. 5, 2020 from U.S. Appl. No. 14/725,174, filed Apr. 29, 2020, 9 pp.
Notice of Reasons for Rejection, and English translation thereof, from counterpart Japanese Application No. 2019-153694, dated Sep. 11, 2020, 15 pp.
First Office Action and Search Report, and translation thereof, from counterpart Chinese Application No. 202110183849.7 dated Jun. 24, 2022, 26 pp.

\* cited by examiner

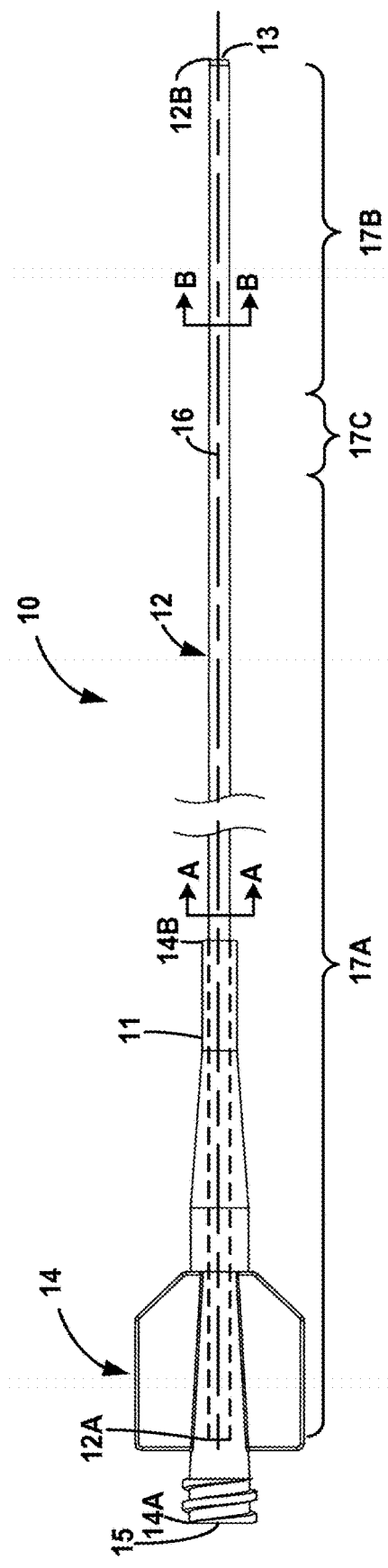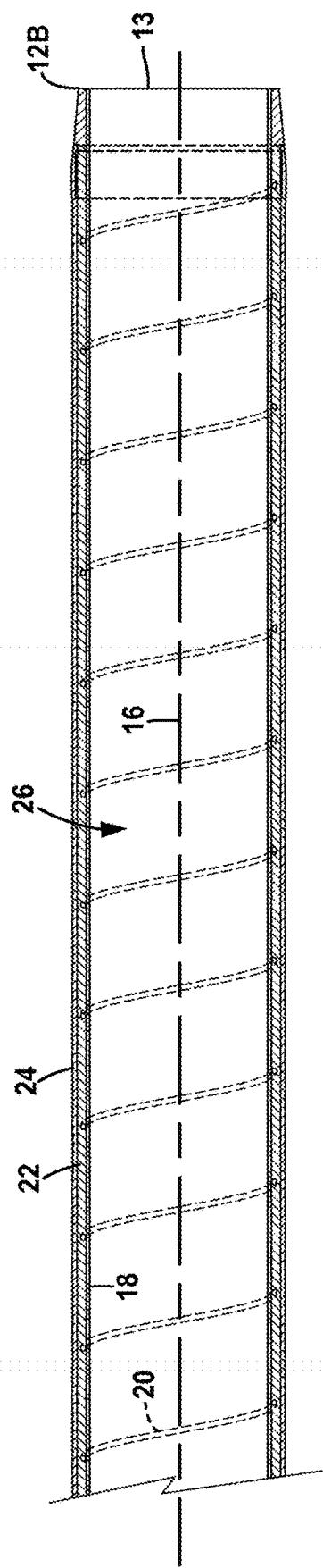
FIG. 1
FIG. 2

CATHETER

This application is a continuation of U.S. application Ser. No. 14/725,108, filed on May 29, 2015, and entitled, "CATHETER WITH TAPERING OUTER DIAMETER," the entire content of which is incorporated herein by reference.

TECHNICAL FIELD

This disclosure relates to a medical catheter.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

In some aspects, this disclosures describes examples catheters that include an outer jacket that comprises a first section decreasing in durometer along a length of the first section in a direction towards a distal end of a catheter body, and a second section more distal than the first section and including the distal end of the elongated body, the second section having a higher durometer than a distal portion of the first section. The second section and an inner liner of the catheter body may define a distal opening of the elongated body configured to resist geometric deformation when the distal end of the catheter body is engaged with a guidewire. This disclosure also describes example methods of forming catheters and methods of using catheters.

Clause 1: In one example, a catheter includes an elongated body extending between a proximal end and a distal end, the elongated body comprising an inner liner defining an inner lumen of the elongated body, an outer jacket, and a structural support member positioned between at least a portion of the inner liner and the outer jacket. The outer jacket comprise a first section decreasing in durometer along a length of the first section in a direction towards the distal end of the elongated body, and a second section more distal than the first section and including the distal end of the elongated body, the second section having a higher durometer than a distal portion of the first section. The second section and the inner liner define a distal opening of the elongated body configured to resist geometric deformation when the distal end of the elongated body is engaged with a guidewire.

Clause 2: In some examples of the catheter of clause 1, the structural support member extends along the first section of the outer jacket and does not extend along the second section.

Clause 3: In some examples some examples of the catheter of clause 1 or 2, a distal tip of the elongated body including the distal end of the elongated body consists essentially of the inner liner and the outer jacket.

Clause 4: In some examples of the catheter of any of clauses 1-3, the catheter further comprises a radiopaque marker coupled to the elongated body, wherein the elongated body distal to the radiopaque marker consists essentially of the inner liner and the outer jacket.

Clause 5: In some examples of the catheter of any of clauses 1-4, the first section of the outer jacket comprises a first segment having a first durometer of 72D, a second segment having a second durometer of 63D, a third segment having a third durometer of 55D, a fourth segment having a fourth durometer of 40D, a fifth segment having a fifth durometer of 35D, and a sixth segment having a sixth durometer of 25D. In these examples, the first segment is axially adjacent to the second segment, the second segment is axially adjacent to and between the first and third segments, the third segment is axially adjacent to and between the second and fourth segments, the fourth segment is axially adjacent to and between the third and fifth segments, and the fifth segment is axially adjacent to and between the fourth and sixth segments. In addition, in these examples, the second section of the outer jacket may have a seventh durometer greater than 25D.

Clause 6: In some examples of the catheter of clause 5, the seventh durometer is 55D.

Clause 7: In some examples of the catheter of any of clauses 1-6, the first section of the outer jacket comprises a plurality of axially adjacent sleeves of decreasing durometer.

Clause 8: In some examples of the catheter of any of clauses 1-7, the first section of the outer jacket comprises a plurality of axially adjacent sleeves, at least two of the sleeves being made from different materials.

Clause 9: In some examples of the catheter of clause 8, a first sleeve of the first section of the outer jacket is formed from aliphatic polyamide and a second sleeve of the second section of the outer jacket is formed from polyether block amide.

Clause 10: In some examples of the catheter of any of clauses 1-9, the structural support member comprises a coil member.

Clause 11: In some examples of the catheter of any of clauses 1-10, the structural support member comprises a hypotube.

Clause 12: In some examples of the catheter of any of clauses 1-11, the structural support member comprises a braided member.

Clause 13: In some examples of the catheter of any of clauses 1-12, the elongated body decreases in diameter from the proximal end to the distal end.

Clause 14: In some examples of the catheter of any of clauses 1-13, an outer diameter of the second section of the outer jacket tapers towards a distal end of the elongated body.

Clause 15: In some examples of the catheter of any of clauses 1-14, the second section has a higher durometer than a distal-most segment of the first section.

Clause 16: In some examples, a catheter comprises an elongated body defining a lumen and extending between a proximal end and a distal end, the elongated body comprising an inner liner defining an inner lumen of the elongated body and extending toward the distal end of the elongated body, a structural support member, and an outer jacket extending to the distal end of the elongated body, the structural support member being positioned between the inner liner and the outer jacket. The outer jacket comprises a proximal segment at the proximal end of the elongated body, a distal segment at a distal end of the elongated body, and a medial segment between the proximal portion and the distal portion, the distal segment having a durometer greater than a durometer of the medial segment.

Clause 17: In some examples of the catheter of clause 16, the structural support member is coextensive with the medial segment of the outer jacket and is not coextensive with the distal segment.

Clause 18: In some examples of the catheter of clause 16 or 17, a distal portion of the elongated body including the distal end of the elongated body consists essentially of the inner liner and the outer jacket.

Clause 19: In some examples of the catheter of any of clauses 16-18, the catheter further comprises a radiopaque marker coupled to the elongated body, wherein the elongated body distal to the radiopaque marker consists essentially of the inner liner and the outer jacket.

Clause 20: In some examples of the catheter of any of clauses 16-19, the proximal segment of the outer jacket comprises a plurality of axially adjacent sleeves of decreasing durometer.

Clause 21: In some examples of the catheter of any of clauses 16-20, the elongated body decreases in diameter from the proximal end to the distal end.

Clause 22: In some examples of the catheter of any of clauses 16-21, an outer diameter of the distal segment of the outer jacket tapers towards a distal end of the elongated body.

Clause 23: In some examples, a method comprises introducing a guidewire in a patient and introducing a catheter in the patient over the guidewire. The catheter comprises an elongated body extending between a proximal end and a distal end, the elongated body comprising an inner liner defining an inner lumen of the elongated body and extending to the distal end of the elongated body, a structural support member, and an outer jacket, the structural support member being positioned between at least a portion of the inner liner and the outer jacket. The outer jacket comprises a first section decreasing in durometer along a length of the first section in a direction towards the distal end of the elongated body and a second section including the distal end of the elongated body, the second section having a higher durometer than a distal portion of the first section. The second section and the inner liner define a distal opening of the elongated member configured to resist geometric deformation when the distal end of the elongated body is engaged with the guidewire.

Clause 24: In some examples, the method of clause 23 further comprises removing a thrombus with the catheter.

Clause 25: In some examples of the method of clause 24, removing the thrombus comprises aspirating the thrombus with the catheter.

Clause 26: In some examples, the method of any of clauses 23-25 further comprises advancing a distal end of the catheter into an intracranial blood vessel.

Clause 27: In some examples, the method of clause 26 further comprises removing a thrombus from the intracranial blood vessel with the catheter.

Clause 28: In some examples, a method comprises forming an elongated body of a catheter, the elongated body extending between a proximal end and a distal end, wherein forming the elongated body comprises positioning a structural support member around at least a portion of an inner liner, the inner liner defining an inner lumen of the elongated body, and positioning an outer jacket over the structural support member and the inner liner. The outer jacket comprises a first section decreasing in durometer along a length of the first section in a direction towards the distal end of the elongated body, and a second section more distal than the first section and including the distal end of the elongated body, the second section having a higher durometer than a distal portion of the first section. The second section and the inner liner define a distal opening of the elongated member configured to resist geometric deformation when the distal end of the elongated body is engaged with a guidewire.

Clause 29: In some examples of the method of clause 28, positioning the outer jacket over the structural support member and the inner liner comprises positioning a first sleeve corresponding to the first section over the structural support member and the inner liner, and positioning a second sleeve corresponding to the second section over the structural support member and the inner liner, distal to the first sleeve.

Clause 30: In some examples, the method of clause 29 further comprises welding the second sleeve to the first sleeve.

Clause 31: In some examples, a method comprises introducing a guidewire in a patient, and introducing a catheter in the patient over the guidewire, the catheter comprising an elongated body extending between a proximal end and a distal end. The elongated body comprises an inner liner defining an inner lumen of the elongated body and extending toward the distal end of the elongated body, a structural support member, and an outer jacket, the structural support member being positioned between at least a portion of the inner liner and the outer jacket. The outer jacket comprises a first section decreasing in durometer along a length of the first section in a direction towards the distal end of the elongated body, and a second section including the distal end of the elongated body, the second section having a higher durometer than a distal portion of the first section, wherein the second section and the inner liner define a distal opening of the elongated member. The method further comprises forming a curve in the guidewire and advancing the catheter over the curve in the guidewire, the distal opening of the catheter resisting geometric deformation when the catheter is advanced over the curve to a greater degree than would occur if the second section were formed of the material of the distal portion of the first section.

Clause 32: In some examples, the method of clause 31 further comprises aspirating thrombus with the catheter.

Clause 33: In some examples, the method of clause 31 or 32 further comprises advancing a distal end of the catheter into an intracranial blood vessel.

Clause 34: In some examples, the method of clause 33 further comprises removing thrombus from the intracranial blood vessel with the catheter.

Clause 35: In some examples, in the method of clause 34, removing thrombus from the intracranial blood vessel with the catheter comprises aspirating the thrombus.

Clause 36: In some examples of the method of any of clauses 31-36, the second section has a higher durometer than a distal-most portion of the first section.

Clause 37: In some examples, a method comprises providing a catheter, the catheter comprising an elongated body extending between a proximal end and a distal end, the elongated body comprising an inner liner defining an inner lumen of the elongated body and extending toward the distal end of the elongated body, a structural support member, and an outer jacket, the structural support member being positioned between at least a portion of the inner liner and the outer jacket. The outer jacket comprises a first section decreasing in durometer along a length of the first section in a direction towards the distal end of the elongated body and a second section including the distal end of the elongated body, the second section having a higher durometer than a distal portion of the first section. The second section and the inner liner define a distal opening of the elongated member. The method further comprises forming a curve in a guidewire and advancing the catheter over the curve in the guidewire, the distal opening of the catheter resisting geometric deformation when the catheter is advanced over the curve to a greater degree than would occur if the second section were formed of the material of the distal portion of the first section.

Clause 38: In some examples of the method of clause 37, the second section has a higher durometer than a distal-most portion of the first section.

Clause 39: In some examples, a method of forming a catheter comprises positioning an inner liner over a first portion, a second portion, and a third portion of a mandrel, the first portion having a first diameter, the second portion having a second diameter less than the first diameter, and the third portion having a tapering diameter that tapers from the first diameter to the second diameter, the third portion being located between the first and second portions; positioning a structural support member over the inner liner, wherein the structural support member, prior to being positioned over the inner liner, tapers in diameter along at least a portion of a length of the structural support member; and positioning an outer jacket over the structural support member.

Clause 40: In some examples of the method of clause 39, positioning the inner liner over the mandrel comprises stretching the inner liner over the mandrel so that the inner liner substantially conforms to the mandrel.

Clause 41: In some examples of the method of clause 39 or 40, positioning the inner liner over the mandrel comprises heat shrinking the inner liner onto the mandrel.

Clause 42: In some examples of the method of any of clauses 39-41, positioning the inner liner over the mandrel comprises stretching the inner liner over the mandrel so that the inner liner substantially conforms to the mandrel and heat shrinking the inner liner onto the mandrel.

Clause 43: In some examples of the method of any of clauses 39-42, the method includes positioning only one inner liner over the mandrel.

Clause 44: In some examples of the method of clause 43, the inner liner is seamless.

Clause 45: In some examples of the method of any of clauses 39-44, after the inner liner is positioned over the mandrel, an inner diameter of the inner liner tapers from the first diameter to the second diameter.

Clause 46: In some examples of the method of any of clauses 39-45, the structural support member comprises a coil member, and the method further comprises forming the coil member prior to positioning the coil member over the inner liner, wherein forming the coil member comprises winding a wire onto a second mandrel into a coil configuration, and heat-setting the wire into the coil configuration, the heat-set wire defining the coil member.

Clause 47: In some examples of the method of clause 46, positioning the structural support member over the inner liner comprises positioning only one coil member over the outer surface of the inner liner before positioning the outer jacket over the structural support member Clause 48: In some examples of the method of clause 47, the only one coil member is devoid of any joints.

Clause 49: In some examples of the method of any of clauses 39-48, the structural support member is a single coil member that changes in pitch along a length of the coil member.

Clause 50: In some examples of the method of any of clauses 39-49, the third portion of the mandrel has a length of about 2.5 centimeters to about 7.6 centimeters.

Clause 51: In some examples of the method of any of clauses 39-50, the mandrel is formed from polytetrafluoroethylene.

Clause 52: In some examples of the method of any of clauses 39-51, the method further comprises applying a thermoset adhesive to an outer surface of the inner liner, wherein positioning the structural support member over the inner liner comprises positioning the structural support member over the outer surface of the inner liner after applying the thermoset adhesive to the outer surface, and curing the thermoset adhesive to adhere the structural support member to the inner liner, wherein positioning the outer jacket over the structural support member comprises positioning the outer jacket over the structural support member after curing the thermoset adhesive.

Clause 53: In some examples of the method of clause 52, the method further comprises heat shrinking the outer jacket over the structural support member and the inner liner, wherein the thermoset adhesive does not adhere the outer jacket to the structural support member after the outer jacket is heat shrunk over the structural support member and the inner liner.

Clause 54: In some examples of the method of clause 53, the thermoset adhesive does not melt during the heat shrinking of the outer jacket over the structural support member and the inner liner.

Clause 55: In some examples of the method of clause 52, the thermoset adhesive comprises a urethane adhesive.

Clause 56: In some examples of the method of clause 52, the structural support member is a single coil member, and wherein curing the thermoset adhesive adheres only the single coil member to the inner liner.

Clause 57: In some examples of the method of any of clauses 39-56, the method further comprises applying a thermoset adhesive to an outer surface of an inner liner to define an adhesive layer having a first thickness less than or equal to a second thickness of the structural support member, wherein positioning the structural support member over the inner liner comprises positioning the coil member over the outer surface of the inner liner after applying the thermoset adhesive to the outer surface.

Clause 58: In some examples of the method of any of clauses 39-57, positioning the outer jacket over the structural support member comprises positioning a plurality of outer jacket segments having different durometers over the structural support member.

Clause 59: In some examples of the method of any of clauses 39-58, positioning the outer jacket over the structural support member comprises positioning a plurality of outer jacket segments formed from different materials over the structural support member.

Clause 60: In some examples of the method of any of clauses 39-59, the method further comprises positioning a marker band over the inner liner distal to a distal end of the structural support member.

Clause 61: In some examples of the method of clause 60, the method further comprises positioning a distal outer jacket segment over the inner liner distal to the marker band and the structural support member.

Clause 62: In some examples of the method of any of clauses 39-61, the method further comprises curing an assembly comprising the inner liner, the structural support member positioned over the inner liner, and the outer jacket.

Clause 63: In some examples of the method of any of clauses 39-62, the method further comprises forming a catheter, wherein forming the catheter comprises positioning the inner liner over the first portion, the second portion, and the third portion of the mandrel, positioning the structural support member over the inner liner, and positioning the outer jacket over the structural support member, and connecting a hub to a proximal end of the catheter, the proximal end of the catheter having a greater diameter than the distal end of the catheter.

Clause 64: In some examples, a method comprises forming a coil member, the coil member tapering in diameter along at least a portion of a length of the coil member, and forming a catheter that includes the coil member, wherein forming the catheter comprises positioning an inner liner over a mandrel, the mandrel tapering from a first diameter to a second diameter less than the first diameter, winding the formed coil member over the inner liner, and positioning an outer jacket over the coil member.

Clause 65: In some examples of the method of clause 64, forming the coil member comprises winding a wire onto a second mandrel into a coil configuration, and heat-setting the wire into the coil configuration, the heat-set wire defining the coil member.

Clause 66: In some examples of the method of clause 64 or 65, positioning the coil member over the inner liner comprises positioning only the coil member over the inner liner before positioning the outer jacket over the structural support member, the coil member being devoid of any joints.

Clause 67: In some examples of the method of any of clauses 64-66, forming the coil member comprises forming the coil member to have a changing a pitch along a length of the coil member.

Clause 68: In some examples of the method of any of clauses 64-67, positioning the inner liner over the mandrel comprises stretching the inner liner over the mandrel so that the inner liner substantially conforms to the mandrel, and heat shrinking the inner liner onto the mandrel.

Clause 69: In some examples of the method of any of clauses 64-68, the inner liner is seamless.

Clause 70: In some examples of the method of any of clauses 64-69, the method further comprises applying a thermoset adhesive to an outer surface of an inner liner, wherein positioning the coil member over the inner liner comprises positioning the coil member over the outer surface of the inner liner after applying the thermoset adhesive to the outer surface, and curing the thermoset adhesive to adhere the coil member to the inner liner, wherein positioning the outer jacket over the coil member comprises positioning the outer jacket over the structural support member after curing the thermoset adhesive.

Clause 71: In some examples, an assembly for forming a catheter comprises a mandrel comprising a first portion having a first diameter, a second portion having a second diameter less than the first diameter, and a third portion having a tapering diameter that tapers from the first diameter to the second diameter, the third portion being located between the first and second portions; a seamless inner liner positioned over the first portion, the second portion, and the third portion of the mandrel and substantially conforming to an outer surface of the mandrel; and a structural support member positioned over the inner liner.

Clause 72: In some examples of the assembly of clause 71, the structural support member is a coil member.

Clause 73: In some examples of the assembly of clause 72, wherein the coil member is devoid of any joints.

Clause 74: In some examples of the assembly of any of clauses 71-73, the mandrel is formed from polytetrafluoroethylene.

Clause 75: In some examples of the assembly of any of clauses 71-74, the assembly further comprises a layer of thermoset adhesive positioned between the structural support member and the inner liner, the layer having a first thickness less than or equal to a second thickness of the structural support member.

Clause 76: In some examples of the assembly of any of clauses 71-75, the assembly further comprises an outer jacket positioned over the structural support member.

Clause 77: In some examples of the assembly of clause 76, the outer jacket comprises a plurality of outer jacket segments formed from different materials.

Clause 78: In some examples of the assembly of clause 77, the outer jacket comprises a plurality of outer jacket segments having different durometers.

Clause 79: In some examples of the assembly of any of clauses 71-78, the assembly further comprises a marker band positioned over the inner liner distal to a distal end of the structural support member.

Clause 80: In some examples of the assembly of clause 79, the assembly further comprises an outer jacket positioned over the structural support member, the outer jacket comprising a distal tip segment positioned over the inner liner distal to the marker band and the structural support member.

Clause 81: In some examples, a catheter comprises an elongated body comprising an inner liner defining an inner lumen of the elongated body, an outer jacket, and a coil member positioned between at least a portion of the inner liner and the outer jacket, wherein the coil member is adhered to the inner liner with a thermoset adhesive, and wherein the coil member and the inner liner are not adhered to the outer jacket.

Clause 82: In some examples of the catheter of clause 81, the thermoset adhesive is not positioned between the coil member and the outer jacket.

Clause 83: In some examples of the catheter of clause 82, substantially no adhesive is present between the coil member and the outer jacket.

Clause 84: In some examples of the catheter of clause 82, substantially no material is present between the coil member and the outer jacket.

Clause 85: In some examples of the catheter of any of clauses 81-84, the thermoset adhesive comprises a urethane adhesive.

Clause 86: In some examples of the catheter of any of clauses 81-85, the outer jacket comprises a plurality of segments having different durometers.

Clause 87: In some examples of the catheter of clause 86, the outer jacket segments are situated longitudinally adjacent to each other.

Clause 88: In some examples of the catheter of any of clauses 81-87, the outer jacket comprises a plurality of segments formed from different materials.

Clause 89: In some examples of the catheter of clause 88, the outer jacket segments are situated longitudinally adjacent to each other.

Clause 90: In some examples of the catheter of any of clauses 81-89, the outer jacket comprises a heat-shrinkable material, the outer jacket being heat shrunk over the inner liner and the coil member.

Clause 91: In some examples of the catheter of any of clauses 81-90, the elongated body tapers from at least a proximal portion having a first outer diameter to a distal portion having a second outer diameter smaller than the first diameter.

Clause 92: In some examples of the catheter of clause 91, the coil member tapers from a first coil diameter to the second coil diameter.

Clause 93: In some examples of the catheter of clause 91, the first outer diameter is about 6 French and the second outer diameter is about 5 French.

Clause 94: In some examples of the catheter of clause 91, the first outer diameter is about 4 French and the second outer diameter is about 3 French.

Clause 95: In some examples of the catheter of any of clauses 81-94, the elongated body has only one coil member.

Clause 96: In some examples of the catheter of any of clauses 81-95, the coil member comprises a nickel titanium alloy.

Clause 97: In some examples of the catheter of any of clauses 81-96, the inner liner comprises polytetrafluoroethylene.

Clause 98: In some examples, a catheter comprises an elongated body comprising an inner liner defining an inner lumen of the elongated body, an outer jacket, and a coil member positioned between at least a portion of the inner liner and the outer jacket, wherein the coil member is adhered to the inner liner with a thermoset adhesive, and wherein the elongated body is devoid of any adhesive between the coil member and the outer jacket.

Clause 99: In some examples of the catheter of clause 98, the elongated body is substantially devoid of any material between the outer surface of the coil member and the inner surface of the outer jacket.

Clause 100: In some examples of the catheter of clause 98 or 99, the thermoset adhesive comprises a urethane adhesive.

Clause 101: In some examples of the catheter of any of clauses 98-100, the outer jacket comprises a plurality of segments having different durometers.

Clause 102: In some examples of the catheter of clause 101, the outer jacket segments are situated longitudinally adjacent to each other.

Clause 103: In some examples of the catheter of any of clauses 98-102, the outer jacket comprises a plurality of segments formed from different materials.

Clause 104: In some examples of the catheter of clause 103, the outer jacket segments are situated longitudinally adjacent to each other.

Clause 105: In some examples of the catheter of any of clauses 98-104, the elongated body tapers from at least a proximal portion having a first outer diameter to a distal portion having a second outer diameter smaller than the first diameter.

Clause 106: In some examples of the catheter of clause 105, wherein the coil member tapers from a first coil diameter to a second coil diameter.

Clause 107: In some examples of the catheter of clause 105, the first outer diameter is about 6 French and the second outer diameter is about 5 French.

Clause 108: In some examples of the catheter of clause 105, the first outer diameter is about 4 French and the second outer diameter is about 3 French.

Clause 109: In some examples of the catheter of any of clauses 98-108, the elongated body has only one coil member.

Clause 110: In some examples, a method comprises applying a thermoset adhesive to an outer surface of an inner liner, positioning a coil member over the outer surface of the inner liner, curing the thermoset adhesive to adhere the coil member to the inner liner, and, after curing the thermoset adhesive, positioning an outer jacket directly over the coil member.

Clause 111: In some examples of the method of clause 110, the method further comprises heat shrinking the outer jacket to the coil member and the inner liner, wherein the thermoset adhesive does not adhere the outer jacket to the coil member after the outer jacket is heat shrunk over the coil member and the inner liner.

Clause 112: In some examples of the method of clause 111, the thermoset adhesive does not melt during the heat shrinking of the outer jacket over the coil member and the inner liner.

Clause 113: In some examples of the method of any of clauses 110-112, positioning the coil member over the outer surface of the inner liner comprises winding the coil member over the outer surface of the inner liner.

Clause 114: In some examples of the method of any of clauses 110-113, the thermoset adhesive comprises a urethane adhesive.

Clause 115: In some examples of the method of any of clauses 110-114, positioning the outer jacket directly over the coil member comprises positioning a plurality of outer jacket segments having different durometers directly over the coil member.

Clause 116: In some examples of the method of any of clauses 110-115, positioning the outer jacket directly over the coil member comprises positioning a plurality of outer jacket segments formed from different materials directly over the coil member.

Clause 117: In some examples of the method of clause 116, the method further comprises positioning the outer jacket segments longitudinally adjacent to each other.

Clause 118: In some examples of the method of any of clauses 110-117, the method further comprises positioning an inner liner over a mandrel, wherein the mandrel tapers from at least a proximal portion having a first outer diameter to a distal portion having a second outer diameter smaller than the first outer diameter.

Clause 119: In some examples of the method of clause 118, the coil member tapers from a first coil diameter to a second coil diameter.

Clause 120: In some examples of the method of clause 118, the first outer diameter is about 6 French and the second outer diameter is about 5 French.

Clause 121: In some examples of the method of clause 118, the first outer diameter is about 4 French and the second outer diameter is about 3 French.

Clause 122: In some examples of the method of any of clauses 110-121, the coil member is a single coil member, and wherein curing the thermoset adhesive adheres only the single coil member to the inner liner.

Clause 123: In some examples of the method of any of clauses 110-122, the method further comprises heat-setting the coil member without the inner liner present, wherein positioning the coil member over the outer surface of the inner liner comprises winding the heat-set coil member onto the outer surface of the inner liner.

Clause 124: In some examples of the method of clause 123, heat-setting the coil member without the inner liner present comprises heat-setting the coil member on a coil mandrel.

Clause 125: In some examples of the method of clause 124, further comprising removing the heat-set coil member from the coil mandrel before winding the removed, heat-set coil member onto the outer surface of the inner liner.

Clause 126: In some examples of the method of clause 125, removing the heat-set coil member from the coil mandrel comprises unwinding the heat-set coil member from the coil mandrel and winding the heat-set coil member onto a reel or bobbin.

Clause 127: In some examples, a catheter comprises an inner liner defining an inner lumen, an outer jacket, and a structural support member positioned between at least a portion of the inner liner and the outer jacket, wherein the inner liner, the outer jacket, and the structural support member define an elongated body extending between a proximal end and a distal end, the elongated body comprising a proximal portion having a first outer diameter, a distal portion having a second outer diameter less than the first outer diameter, the distal portion including the distal end of the elongated body, and a medial portion positioned between the proximal portion and the distal portion, the medial portion tapering from the first outer diameter to the second outer diameter.

Clause 128: In some examples of the catheter of clause 127, the proximal portion includes the proximal end of the elongated body.

Clause 129: In some examples of the catheter of clause 127 or 128, the medial portion has a length of about 2.5 centimeters to about 7.6 centimeters.

Clause 130: In some examples of the catheter of any of clauses 127-129, only one structural support member is positioned between the outer jacket and the inner liner.

Clause 131: In some examples of the catheter of clause 130, the structural support member is a single coil that progressively changes in pitch as it extends distally through the elongated body.

Clause 132: In some examples of the catheter of clause 131, the structural support member is a single coil that tapers in diameter along the medial portion.

Clause 133: In some examples of the catheter of clause 130, the structural support member is a single coil that tapers in diameter along the medial portion.

Clause 134: In some examples of the catheter of clause 133, the single coil is devoid of any joints.

Clause 135: In some examples of the catheter of any of clauses 127-134, the catheter has only one inner liner.

Clause 136: In some examples of the catheter of clause 135, the inner liner is seamless.

Clause 137: In some examples of the catheter of clause 135, the inner liner tapers through the medial portion of the elongated body from a first inner diameter in the proximal portion of the elongated body to a second inner diameter in the distal portion of the elongated body, the second inner diameter being less than the first inner diameter.

Clause 138: In some examples of the catheter of clause 135, an inner diameter of the inner liner is substantially constant.

Clause 139: In some examples of the catheter of clause 135, the inner liner comprises polytetrafluoroethylene.

Clause 140: In some examples of the catheter of any of clauses 127-139, the outer jacket comprises a plurality of sections having different durometers.

Clause 141: In some examples of the catheter of any of clauses 127-140, the outer jacket comprises a plurality of sections formed from different materials.

Clause 142: In some examples of the catheter of any of clauses 127-141, the outer jacket comprises a heat-shrinkable material, the outer jacket being heat shrunk over the inner liner and the coil member.

Clause 143: In some examples of the catheter of any of clauses 127-142, at least a part of the proximal portion adjacent to the medial portion has a constant outer diameter substantially equal to the first outer diameter.

Clause 144: In some examples of the catheter of any of clauses 127-143, at least a part of the distal portion adjacent to the medial portion has a constant outer diameter substantially equal to the second outer diameter.

Clause 145: In some examples of the catheter of any of clauses 127-144, the first diameter is about 6 French and the second diameter is about 5 French.

Clause 146: In some examples of the catheter of any of clauses 127-144, the first diameter is about 4 French and the second diameter is about 3 French.

Clause 147: In some examples of the catheter of any of clauses 127-146, the elongated body is a unitary body devoid of any joints between the proximal, medial, and distal portions.

Clause 148: In some examples, a catheter comprises a seamless inner liner extending between a proximal end and a distal end, the inner liner defining an inner lumen, an outer jacket, and a coil member positioned between at least a portion of the seamless inner liner and the outer jacket, wherein the seamless inner liner, the outer jacket, and the coil member define an elongated body tapering from a first outer diameter at a proximal portion to a second outer diameter at a distal portion, the second outer diameter being less than the first outer diameter, and wherein the proximal portion includes the proximal end of the seamless inner liner and the distal portion includes the distal end of the seamless inner liner.

Clause 149: In some examples of the catheter of clause 148, the elongated body further comprises a medial portion positioned between the proximal portion and the distal portion, the medial portion tapering from the first diameter to the second diameter.

Clause 150: In some examples of the catheter of clause 149, the coil member progressively changes in pitch in the medial portion.

Clause 151: In some examples of the catheter of any of clauses 148-150, the proximal and distal portions each have a constant outer diameter.

Clause 152: In some examples of the catheter of any of clauses 148-151, only one coil member is positioned between the outer jacket and the inner liner, the coil member tapering in diameter and devoid of any joints.

Clause 153: In some examples of the catheter of clause 152, the coil member progressively changes in pitch as it extends distally through the elongated body.

Clause 154: In some examples of the catheter of any of clauses 148-153, the seamless inner liner tapers from a first inner diameter in the proximal portion of the elongated body to a second inner diameter in the distal portion of the elongated body, the second inner diameter being less than the first inner diameter Clause 155: In some examples of the catheter of any of clauses 148-154, an inner diameter of the inner liner is substantially constant.

Clause 156: In some examples, a method comprises positioning an inner liner over a mandrel, positioning a structural support member over an outer surface of the inner liner, and positioning an outer jacket over the structural support member, wherein the inner liner, the outer jacket, and the structural support member define an elongated body extending between a proximal end and a distal end, the elongated body comprising a proximal portion having a first outer diameter, a distal portion having a second outer diameter less than the first outer diameter, the distal portion including the distal end of the elongated body, and a medial portion positioned between the proximal portion and the distal portion, the medial portion tapering from the first outer diameter to the second outer diameter.

Clause 157: In some examples of the method of clause 156, positioning the inner liner over the mandrel comprises heat shrinking the inner liner onto the mandrel.

Clause 158: In some examples of the method of clause 156 or 157, positioning the inner liner over the mandrel comprises stretching the inner liner over the mandrel so that the inner liner substantially conforms to the mandrel.

Clause 159: In some examples of the method of any of clauses 156-158, the mandrel tapers from a third diameter to a fourth diameter, the fourth diameter being less than the third diameter.

Clause 160: In some examples of the method of clause 159, the structural support member tapers from the third diameter to the fourth diameter prior to being positioned over the outer surface of the inner member.

Clause 161: In some examples of the method of any of clauses 156-160, positioning the structural support member over the outer surface of the inner liner comprises winding a coil member over the outer surface of the inner liner.

Clause 162: In some examples of the method of any of clauses 156-161, the proximal portion includes the proximal end of the elongated body.

Clause 163: In some examples of the method of any of clauses 156-162, the medial portion has a length of about 2.5 centimeters to about 7.6 centimeters.

Clause 164: In some examples of the method of any of clauses 156-163, positioning the structural support member over the outer surface of the inner liner comprises positioning only one structural support member over the outer surface of the inner liner before positioning the outer jacket over the structural support member.

Clause 165: In some examples of the method of any of clauses 156-164, the structural support member is a single coil that progressively changes in pitch as it extends distally through the medial portion of the elongated body.

Clause 166: In some examples of the method of clause 165, a first pitch of the single coil in the proximal portion of the elongated body is about 0.00225 inches (about 0.057 mm), a second pitch of the single coil in the medial portion of the elongated body is about 0.00250 inches (about 0.064 mm), a third pitch of the single coil in the distal portion of the elongated body is 0.0030 inches (about 0.076 mm), and a fourth pitch of the single coil in the distal portion of the elongated body is 0.0070 inches (about 0.18 mm).

Clause 167: In some examples of the method of any of clauses 156-166, the structural support member is a single coil member that tapers in diameter along the medial portion prior to being positioned over the outer surface of the inner liner.

Clause 168: In some examples of the method of clause 167, the single coil is devoid of any joints.

Clause 169: In some examples of the method of any of clauses 156-168, the structural member comprises a coil member, and the method further comprises forming the coil member prior to positioning the coil member over the inner liner, wherein forming the coil member comprises winding a wire onto a second mandrel into a coil configuration, and heat-setting the wire into the coil configuration, the heat-set wire defining the coil member.

Clause 170: In some examples of the method of any of clauses 156-169, the method includes positioning only one inner liner over the mandrel.

Clause 171: In some examples of the method of clause 170, the inner liner is seamless.

Clause 172: In some examples of the method of clause 170, after the inner liner is positioned over the mandrel, the inner liner tapers from a first inner diameter to a second inner diameter, the second inner diameter being less than the first inner diameter.

Clause 173: In some examples of the method of any of clauses 156-172, positioning the outer jacket over the coil member comprises positioning a plurality of outer jacket segments having different durometers over the coil member.

Clause 174: In some examples of the method of any of clauses 156-173, positioning the outer jacket over the coil member comprises positioning a plurality of outer jacket segments formed from different materials over the coil member.

Clause 175: In some examples of the method of any of clauses 156-174, the method further comprises heat shrinking the outer jacket to the coil member and the inner liner.

Clause 176: In some examples of the method of any of clauses 156-175, the elongated body is a unitary body devoid of any joints between the proximal, medial, and distal portions.

Clause 177: In some examples of the method of any of clauses 156-176, the method further comprises applying a thermoset adhesive to the outer surface of the inner liner prior to positioning the structural support member over the outer surface of the inner liner.

Clause 178: In some examples of the method of clause 177, the method further comprises curing the thermoset adhesive prior to positioning the outer jacket over the structural support member.

Clause 179: In some examples of the method of clause 178, the structural support member is a single coil member, and wherein curing the thermoset adhesive adheres only the single coil member to the inner liner.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 1 is a side elevation view of an example catheter, which includes a catheter body and a hub.

FIG. 2 is a conceptual cross-sectional view of a part of the catheter body 12 of FIG. 1 including the distal end, where the cross-section taken through a center of the catheter body and along a longitudinal axis of the catheter body.

DETAILED DESCRIPTION

Figure 4:
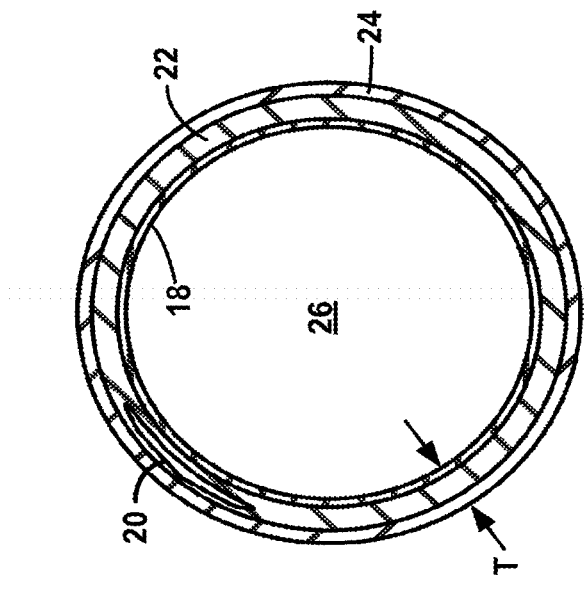
FIG. 4 is a conceptual cross-sectional view of the catheter body of FIG. 1 taken along line B-B in FIG. 1.

In some embodiments, a medical catheter ("catheter") described herein includes a relatively flexible catheter body that is configured to be navigated through vasculature of a patient, e.g., tortuous vasculature in a brain of the patient. The catheter body is configured to exhibit a relatively high level of structural integrity while defining a thin-walled construction. In this way, the catheter may maintain a relatively low profile (e.g., a relatively small outer diameter), while still providing a relatively large inner lumen (also referred to as a working channel in some examples), through which distal tissue sites may be accessed, e.g., to deliver a medical device or therapeutic agent, to remove a thrombus or other target from the patient's body, or any combination thereof.

A relatively small outer diameter catheter body may be easier to navigate through relatively narrow spaces in the patient's body compared to a catheter body having a larger outer diameter. In addition, the relatively large inner diameter of the catheter may provide for more efficient and/or more effective aspiration of thrombus from the vasculature compared to catheter bodies having smaller inner diameters, e.g., due to a larger aspiration force that can be applied to the catheter, due to the larger catheter inner lumen for receiving the thrombus, or both. In addition to, or instead of, providing benefits when used to aspirate a thrombus from the vasculature, the relatively large inner diameter for a given outer diameter may accommodate a larger range of medical devices and a larger range of fluid volumes. Thus, the thin-walled catheter body defining a relatively large inner diameter for a given outer diameter maybe used with a larger range of medical procedures.

In some embodiments, the catheter body includes an inner liner, a structural support member, a support layer, and an outer jacket, which interact to provide a flexible catheter body with sufficient structural integrity (e.g., columnar strength) to permit the catheter body to be advanced through the vasculature from a pushing force applied to a proximal portion of the catheter body, without buckling or undesirable bending (e.g., kinking) of the catheter body. In some examples, the flexible catheter body is configured to substantially conform to the curvature of the vasculature. In addition, in some examples, the catheter body has a columnar strength and flexibility that allow at least a distal portion of the catheter body to be navigated from a femoral artery, through the aorta of the patient, and into the intracranial vascular system of the patient, e.g., to reach a relatively distal treatment site, including the middle cerebral artery (MCA), the Circle of Willis, and tissue sites more distal than the MCA and the Circle of Willis. The MCA and, consequently, vasculature distal to the MCA may be relatively difficult to access due to the carotid siphon or vertebral artery anatomy that must be traversed to reach such locations.

In some cases, a clinician may steer a catheter through the vasculature of a patient by rotating the catheter. A distal portion of the catheter body leads a proximal portion of the catheter body through the vasculature, and may, therefore, be introduced in the patient while the proximal portion is external to the patient. The clinician may apply torque to the proximal portion of the catheter body (or at least a portion of the catheter body that is more proximal than the distal portion implanted in the patient) in order to rotate the distal portion of the catheter. Some embodiments of the catheter body described herein are configured to transmit the torque applied to a relatively proximal portion to a relatively distal portion. The catheter body may be relatively resistant to kinking upon rotation of the catheter body from the relatively proximal portion of the catheter body. For example, the catheter body may include a structural support member (e.g., a helical coil member or a braided member) and a support layer, which are configured to help distribute the torsional forces along the catheter body.

In some examples, the catheter may be a guide catheter that acts as a conduit to help support a microcatheter. In other examples, the catheter may be a microcatheter. In either example, the catheter body of the catheter may define an inner lumen, which may be configured to receive one or more medical devices, deliver a therapeutic agent to a distal tissue site, remove thrombus (e.g., by aspiration) from the patient's vasculature, and the like or any combination thereof. Example therapeutic agents include, but are not limited to, an oxygenated medium or a pharmaceutical agent, which may be, for example, a vasodilator such as nifedipine or sodium nitroprusside, or a tissue plasminogen activator (t-PA), which can be used to breakdown blood clots.

In examples in which the inner lumen defined by the catheter body is used to remove thrombus from vasculature, the catheter may be referred to as an aspiration catheter. A vacuum may be applied to a proximal end of the catheter body to draw a thrombus into the inner lumen. An aspiration catheter may be used in a medical procedure to treat an ischemic insult, which may occur due to occlusion of a blood vessel that deprives brain tissue of oxygen-carrying blood. In some examples, in addition to being configured to be navigated to relatively distal tissue sites, an aspiration catheter may also include a distal tip configuration that is configured to substantially maintain its shape, even in the presence of the vacuum force applied to the catheter during the aspiration process.

The catheters described herein may be advanced to a target location within vasculature of the patient in cooperation with a guidewire, an inner catheter, or both, which may aid in the navigation (e.g., steering and manipulation) of the catheter through the vasculature. For example, an inner lumen of the catheter body may be configured to receive a guidewire or an inner catheter, such that the catheter body may be guided through vasculature over the guidewire or the inner catheter. As described in further detail below, in some examples, a distal tip of the catheter body is configured to resist geometric deformation from forces applied to the distal tip by the guidewire or inner catheter. This resistance to geometric deformation may help improve the ease with which the catheter body may be guided to a relatively distal tissue site, e.g., through relatively tight turns in the vasculature.

Although primarily described as being used to reach relatively distal vasculature sites, the relatively thin-walled and kink resistant catheters described herein may readily be configured to be used with other target tissue sites. For example, the catheters may be used to access tissue sites throughout the coronary and peripheral vasculature, the gastrointestinal tract, the urethra, ureters, Fallopian tubes and other body lumens.

FIG. 1 is a side elevation view of an example catheter 10, which includes catheter body 12 and hub 14. Catheter hub 14 is positioned at a proximal end of catheter 10 and defines an opening through which an inner lumen 26 (shown in FIG. 2) of catheter body 12 may be accessed and, in some examples, closed. For example, catheter hub 14 may include a luer connector for connecting to another device, a hemostasis valve, or another mechanism or combination of mechanisms. In some examples, catheter 10 includes strain relief member 11, which may be a part of hub 14 or may be separate from hub 14. In other examples, the proximal end of catheter 10 can include another structure in addition or, or instead of, hub 14.

Catheter body 12 is an elongated body that extends from proximal end 12A to distal end 12B and defines at least one inner lumen 26 (e.g., one inner lumen, two inner lumens, or three inner lumens) that terminates at distal opening 13 defined by catheter body 12. In the example shown in FIG. 1, proximal end 12A of catheter body 12 is received within hub 14 and is mechanically connected to hub 14 via an adhesive, welding, or another suitable technique or combination of techniques. Opening 15 defined by hub 14 and located at proximal end 14A of hub 14 is aligned with the inner lumen of catheter body 12, such that the inner lumen of catheter body 12 may be accessed via opening 15.

Catheter body 12 has a suitable length for accessing a target tissue site within the patient from a vascular access point. The length may be measured along longitudinal axis 16 of catheter body 12. The target tissue site may depend on the medical procedure for which catheter 10 is used. For example, if catheter 10 is a distal access catheter used to access vasculature in a brain of a patient from a femoral artery access point at the groin of the patient, catheter body 12 may have a length of about 129 centimeters (cm) to about 135 cm, such as about 132 cm, although other lengths may be used.

As described in further detail below, catheter body 12 may be used to access relatively distal locations in a patient, such as the MCA in a brain of a patient. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists and/or turns) through the vasculature to reach these tissue sites. Catheter body 12 may be structurally configured to be relatively flexible, pushable, and relatively kink- and buckle-resistant, so that it may resist buckling when a pushing force is applied to a relatively proximal portion of the catheter to advance the catheter body distally through vasculature, and so that it may resist kinking when traversing around a tight turn in the vasculature. Kinking and/or buckling of catheter body 12 may hinder a clinician's efforts to push the catheter body distally, e.g., past a turn.

One structural characteristic that may contribute to at least the pushability and flexibility of catheter body 12 is the outer diameter of catheter body 12, which tapers from a first outer diameter at a proximal portion 17A to a second outer diameter at a distal portion 17B, the second outer diameter being smaller than the first outer diameter. Proximal portion 17A may include proximal end 12A and distal portion 17B may include distal end 12B. Catheter body 12 may further include a medial portion 17C between proximal portion 17A and distal portion 17B; medial portion 17C may gradually taper in outer diameter from the first outer diameter to the second outer diameter. Thus, medial portion 17C can define a smooth transition from the larger diameter proximal portion 17A to the smaller diameter distal portion 17B. In some examples, medial portion 17C continuously tapers (e.g., a linear rate of change in outer diameter) from the first outer diameter to the second outer diameter. In other examples, medial portion 17C may taper in a curved manner, e.g., defining a convex or concave curve, or it may progressively change in outer diameter, e.g., it may define discrete step-downs in outer diameter to define the taper. The size of the discrete step-downs in diameter may be selected to reduce the number of edges that may catch on anatomical features within the vasculature as catheter body 12 is advanced through vasculature.

In some examples, at least a part (e.g., only part of the length or the entire length) of proximal portion 17A and/or distal portion 17B has a constant outer diameter. For example, the constant outer diameter in proximal portion 17A may be just proximal of medial portion 17C and the constant outer diameter in distal portion 17B may be just distal of medial portion.

A larger diameter proximal portion 17A may provide better proximal support for catheter body 12, which may help increase the pushability of catheter body 12. In contrast, in examples in which a catheter body has a constant diameter along its entire length, the constant diameter may be selected to facilitate distal flexibility of the catheter body 12, and, as a result, may be configured with less proximal support than catheter body 12. Catheter body 12 can have a smaller outer diameter at distal portion 17B to increase the flexibility of catheter body 12 along distal portion 17B, while still maintaining an outer diameter at proximal portion 17A that better facilitates pushability of catheter body 12.

A catheter having a smaller outer diameter may be easier to navigate through tortuous vasculature. Thus, by reducing the outer diameter of catheter body 12 at distal portion 17B, which leads catheter body 12 through vasculature, catheter body 12 may better traverse through tortuous vasculature with still maintaining a relatively high level of proximal pushability. In some cases, proximal portion 17A may not be introduced into low profile or tortuous arteries, such that the cross-sectional size of proximal portion 17A may be increased in favor of proximal support without adversely affecting the ability of catheter body 12 to reach relatively distal tissue sites.

In some examples, the first outer diameter is about 6 French (e.g., 6 French or nearly 6 French) and the second outer diameter is about 5 French (e.g., 5 French or nearly 5 French). In other examples, the first outer diameter is about 4 French (e.g., 4 French or nearly 4 French) and the second outer diameter is about 3 French (e.g., 3 French or nearly 3 French). The measurement term French, abbreviated Fr or F, is three times the diameter of a device as measured in mm. Thus, a 6 French diameter is about 2 millimeters (mm), a 5 French diameter is about 1.67 mm, a 4 French diameter is about 1.33 mm, and a 3 French diameter is about 1 mm.

The proximal, distal, and medial portions 17A-17C of catheter body 12 may each have any suitable length. The working length of catheter body 12 may be measured from distal end 14B of hub 14 to distal end 12B of catheter body 12. In some examples, the length of proximal portion 17A that extends from distal end 14B of hub 14 to medial portion 17C is about 38.16 inches (about 96.93 cm), medial portion 17C has a length of about 1 inch (about 2.5 cm) to about 3 inches (about 7.6 cm), such as about 2 inches (about 5 cm) and distal portion 17B has a length of about 11.1 inches (about 30 cm). However, in other examples, proximal, distal, and medial portions 17A-17C may have different lengths.

The length over which catheter body 12 tapers from the first outer diameter to the second outer diameter, which may be the length of medial portion 17C, may be long enough to provide a relatively smooth transition between the first and second outer diameters. A relatively abrupt transition, such as a taper over 0.5 cm or less, may define a ledge, which may cause catheter body 12 to catch on certain anatomical features as it is advanced through vasculature of the patient. This may adversely affect the navigability of catheter body 12. A relatively abrupt transition may also cause a greater disturbance in the blood flow around catheter body 12 when body 12 is positioned in vasculature compared to a more gradual taper provided by medial portion 12. The flow disturbance may be undesirable in some cases.

In some examples, the diameter of inner lumen 26 (shown in FIG. 2) of catheter body 12, also referred to herein as an inner diameter of catheter body 12, may be substantially constant from proximal end 12A to distal end 12B. In other examples, the inner diameter of catheter body 12 may taper from a first inner diameter at a proximal portion that includes proximal end 12A to a second inner diameter at a distal portion that includes distal end 12B, the second inner diameter being smaller than the first inner diameter. For example, an inner diameter of catheter body 12 may taper from a first inner diameter of about 0.0685 inches (about 1.74 mm) to a second inner diameter of about to 0.0605 inches (about 1.54 mm). The inner diameter may, for example, gradually taper along the portion of inner lumen 26 extending through medial portion 17C of catheter body 12, where the taper can be linear, curved, continuous or discontinuous; e.g., the inner diameter of catheter body 12 may step-down from the first inner diameter to the second inner diameter in discrete steps.

Catheter body 12 can be relatively thin-walled, such that it defines a relatively large inner diameter for a given outer diameter, which may further contribute to the flexibility and kink-resistance of catheter body 12. The wall thickness of catheter body 12 may be the difference between the outer diameter of catheter body 12 and the inner diameter of catheter body 12, as defined by inner lumen 26.

In some examples, rather than being formed from two or more discrete and separate longitudinally extending segments that are mechanically connected to each other, e.g., at axial butt joints, catheter body 12 may be substantially continuous along a length of catheter body 12. For example, catheter body 12 may include an inner liner that defines the inner lumen of catheter body 12 and continuously extends from proximal end 12A to distal end 12B of catheter body 12, and a structural support member that extends across at least a part of the proximal portion, at least part of the distal portion, and the medial portion of catheter body 12. A substantially continuous catheter body 12 may be better configured to better distribute forces in a longitudinal direction (in a direction along longitudinal axis 16) and rotational direction (rotation about longitudinal axis 16) compared to a catheter body including two or more longitudinally extending segments that are mechanically connected to each other. Thus, the substantially continuous construction of catheter body 12 may contribute to the ability of body 12 to transfer axial pushing forces from proximal portion 17A of catheter body 12 to distal portion 17B, as well transfer rotational forces (if any) applied from proximal portion 17A of catheter body 12 to distal portion 17B.

While in some examples, as described with reference to FIG. 5, catheter body 12 includes an outer jacket formed of two or more longitudinally extending segments that are in an abutting relationship, due to the continuous inner liner and the structural support member that extends along a majority of the length of catheter body 12, catheter body 12 may still better distribute forces and flexibility compared to a catheter body including two or more longitudinal sections that are mechanically connected to each other. The inner liner and/or structural support member that extends through at least a part of proximal portion 17A, at least part of distal portion 17B, and medial portion 17C of catheter body 12 may provide sufficient continuity to catheter body 12 to provide it with the desired force distribution characteristics for facilitating pushing of catheter body 12 to relatively distal tissue sites, and for facilitating rotational movement of catheter body 12.

In some examples, at least a portion of an outer surface of catheter body 12 includes one or more coatings, such as, but not limited to, an anti-thrombogenic coating, which may help reduce the formation of thrombi in vitro, an anti-microbial coating, and/or a lubricating coating. The lubricating coating may be configured to reduce static friction and/kinetic friction between catheter body 12 and tissue of the patient as catheter body 12 is advanced through the vasculature. The lubricating coating can be, for example, a hydrophilic coating. In some examples, the entire working length of catheter body 12 (from distal portion 14B of hub 14 to distal end 12B) is coated with the hydrophilic coating. In other examples, only a portion of the working length of catheter body 12 coated with the hydrophilic coating. This may provide a length of catheter body 12 distal to distal end 14B of hub 14 with which the clinician may grip catheter body 12, e.g., to rotate catheter body 12 or push catheter body 12 through vasculature.

Figure 3:
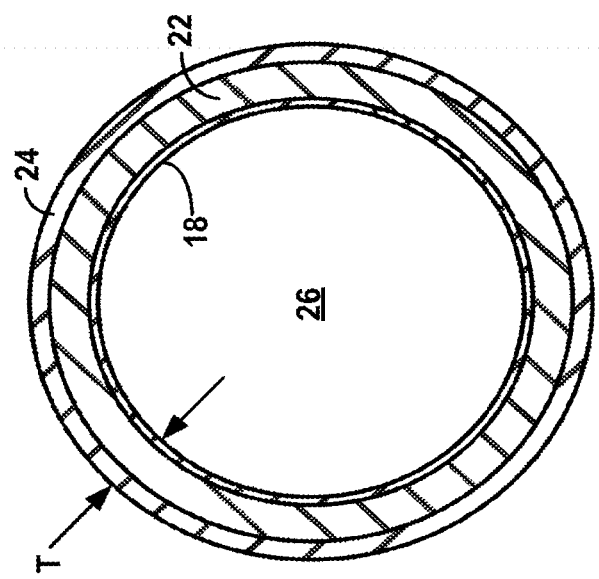
FIG. 3 is a conceptual cross-sectional view of the catheter body of FIG. 1 taken along line A-A in FIG. 1.

FIG. 2 is a conceptual cross-sectional view of a part of catheter body 12 including distal end 12B, where the cross-section is taken through a center of catheter body 12 along longitudinal axis 16. FIG. 3 is a conceptual cross-sectional view of catheter body 12 taken along line A-A in FIG. 1, and FIG. 4 is a conceptual cross-sectional view of catheter body 12 taken along line B-B in FIG. 1. As shown in FIGS. 2-4, catheter body 12 includes inner liner 18, structural support member 20, support layer 22, and outer jacket 24.

Inner liner 18 defines inner lumen 26 of catheter body 12, inner lumen 26 extending from proximal end 12A to distal end 12B and defining a passageway extending from proximal end 12A to distal opening 13 at distal end 12B of catheter body 12. Inner lumen 26 may be sized to receive a medical device (e.g., another catheter, a guidewire, an embolic protection device, a stent, or any combination thereof), a therapeutic agent, or the like. At least the inner surface of inner liner 18 defining inner lumen 26 may be lubricious in some examples in order to facilitate the introduction and passage of a device, a therapeutic agent, or the like, through inner lumen 26. For example, the material from which the entire inner liner 18 is formed may be lubricious, or inner liner 18 may be formed from two or more materials, where the material that defines inner lumen 26 may be more lubricious than the material that interfaces with structural support member 20 and support layer 22. In addition to, or instead of, being formed from a lubricious material, in some examples, an inner surface of inner liner 18 is coated with a lubricious coating.

Example materials from which inner liner 18 may be formed include, but are not limited to, polytetrafluoroethylene (PTFE), fluoropolymer, perfluoroalkyoxy alkane (PFA), fluorinated ethylene propylene (FEP), or any combination thereof. For example, inner liner 18 may be formed from a non-etched PTFE, e.g., may consist essentially of a non-etched PTFE.

In some examples, inner liner 18 is a single, seamless tubular body, such that inner lumen 26 of catheter body 12 is continuous along its entire length, e.g., from proximal end 12A to distal opening 13. A seamless inner liner 18 may, for example, be devoid of any seams (e.g., the seam formed from joining two separate tubular bodies together at an axial location), such that the seamless inner liner 18 is a unitary body, rather than multiple, discrete bodies that are separately formed and subsequently connected together. In addition, in some examples, inner liner 18 defines a substantially constant (e.g., identical or nearly identical) inner diameter along the entire length of inner liner 18, while in other examples, inner liner 18 may define different inner diameters. For example, inner liner 18 may define a first inner diameter along a proximal portion of inner liner 18 and a second inner diameter along a distal portion of inner liner, the second inner diameter being smaller than the first inner diameter. For example, inner liner 18 may taper continuously from the first inner diameter to the second inner diameter, or may define one or more step-downs in inner diameter along the length of inner liner 18. As another example, as described with reference to FIG. 1, inner liner 18 may have a proximal portion having the first inner diameter along proximal portion 17A (FIG. 1) of catheter body 12, a distal portion having the second inner diameter along distal portion 17B (FIG. 1) of catheter body 12, and a medial portion positioned between the proximal and distal portions and gradually tapering from the first inner diameter to the second inner diameter.

In some examples in which inner liner 18 defines inner lumen 26 having different diameters, the wall thickness T (shown in FIGS. 3 and 4) may vary along the length of catheter body 12. For example, the wall thickness T in proximal portion 17A may be greater than wall thickness T in distal portion 17B. In other examples, the wall thickness T may be substantially the same (e.g., identical or nearly identical) along a length of catheter body 12.

A seamless inner liner 18 may be easier to slide over another device, e.g., another catheter or a guidewire, compared to a catheter formed from two or more longitudinal sections that are mechanically connected to each other because the seamless inner liner may define a smoother inner lumen 26. In contrast, joints between sections of an inner liner that are formed from two or more longitudinal sections may define surface protrusions or other irregularities along inner lumen 26 which may interfere with the passage of devices through inner lumen 26. In addition, a seamless inner liner 18 may help distribute pushing and rotational forces along the length of catheter body 12. Thus, the seamless inner liner 18 may help contribute to the pushability of catheter body 12.

Structural support member 20 is configured to increase the structural integrity of catheter body 12 while allowing catheter body 12 to remain relatively flexible. For example, member 20 may be configured to help catheter body 12 substantially maintain its cross-sectional shape or at least help prevent catheter body 12 from buckling or kinking as it is navigated through tortuous anatomy. Structural support member 20, together with inner liner 18, support layer 22, and outer jacket 24, may help distribute both pushing and rotational forces along a length of catheter body 12, which may help prevent kinking of body 12 upon rotation of body 12 or help prevent buckling of body 12 upon application of a pushing force to body 12. As a result, a clinician may apply pushing forces, rotational forces, or both, to a proximal portion of catheter body 12, and such forces may cause a distal portion of catheter body 12 to advance distally, rotate, or both, respectively.

In the example shown in FIGS. 1 and 2, structural support member 20 extends along only a portion of a length of catheter body 12. For example, a proximal end of structural support member 20 may be positioned distal to distal end 14B of hub 14 (and/or of strain relief 11) and a distal end of member 20 be positioned at distal end 12B of catheter 12 or proximal to distal end 12B. In other examples, a proximal end of structural support member 20 may be positioned proximal to distal end 14B of hub 14 and a distal end of member 20 be positioned at distal end 12B of catheter 12 or proximal to distal end 12B.

In some examples, structural support member 20 includes a generally tubular braided structure, a coil member defining a plurality of turns, e.g., in the shape of a helix, or a combination of a braided structure and a coil member. Thus, although examples of the disclosure describe structural support member 20 as a coil, in some other examples, the catheter bodies described herein may include a braided structure instead of a coil or a braided structure in addition to a coil. For example, a proximal portion of structural support member 20 may include a braided structure and a distal portion of structural support member 20 may include a coil member.

Structural support member 20 is coupled, adhered and/or mechanically connected to at least a portion of an outer surface of inner liner 18 via support layer 22. For example, support layer 22 may be a thermoplastic material or a thermoset material, such as a thermoset polymer and/or a thermoset adhesive (e.g., a thermoset polyurethane adhesive, such as Flexobond 430, commercially available from Bacon Industries of Irvine, Calif.). In some cases, the material forming support layer 22 may have elastic properties, such that there may be a tendency for support layer 22 to a return to a resting position. This may be referred to as "bounce back" of support layer 22. A support layer 22 formed from a cured thermoset polyurethane adhesive exhibits a relatively delayed bounce back response compared to a thermoplastic material, e.g., due at least in part to the elastic properties of the thermoset polyurethane adhesive. The delayed bounce back response may be advantageous for navigating catheter body 12 through vasculature. For example, the delayed bounce back response may reduce the extent to which catheter body 12 may spring against vascular walls as it is advanced through the vasculature.

In some examples, support layer 22 is positioned between the entire length of structural support member 20 and inner liner 18. In other examples, support layer 22 is only positioned between a part of the length of structural support member 20 and inner liner 18.

In some examples, as shown in FIG. 4, support layer 22 may only be positioned between structural support member 20 and inner liner 18, and substantially no support layer 22 material (e.g., no support layer material or nearly no support layer material) is positioned between structural support member 20 and outer jacket 24. As a result, support member 20 and inner liner 18 are not adhered to outer jacket 24 via support layer 22. For example, in some examples, as described in further detail with respect to FIGS. 8 and 9, when support layer 22 comprises a thermoset polymer, the polymer may be cured before outer jacket 24 is positioned over inner liner 18 and structural support member 20. Due to the relatively high melting temperature of the thermoset polymer, as well as other properties of the thermoset polymer (compared to thermoplastic materials), outer jacket 24 may be heat shrunk onto structural support member 20 and support layer 22 without causing the thermoset polymer to melt and reflow. As a result, the relative position between structural support member 20 and inner liner 18 may be maintained during the one or more manufacturing steps in which outer jacket 24 is mechanically connected to structural support member 20 and support layer 22.

The use of a thermoset polymer to mechanically connect structural support member 20 to inner liner 18 may help reduce or minimize the amount of (or eliminate entirely) material between structural support member 20 and outer jacket 24, which further contributes to the thinness of the walls of catheter body 12. For example, outer jacket 24 may be heat shrunk onto structural support member 20 and support layer 22, which may eliminate the need for an adhesive to further mechanically connect outer jacket 24 to structural support member 20 and support layer 22. As a result, structural support member 20 and inner liner 18 may not be adhered to outer jacket 24. In at least this way, the use of a thermoset polymer between member 20 and inner liner 18 may help eliminate an adhesive layer between member 20 and outer jacket 24, which may help reduce the wall thickness T (shown in FIGS. 3 and 4) of catheter body 12 and, therefore, increase the inner diameter of catheter body 12 for a given outer diameter.

Reducing the thickness of the catheter body wall may help increase the inner diameter of inner lumen 26 for a given outer diameter of catheter body 12. As discussed, a larger inner lumen 26 may provide certain benefits in some examples, such as allowing for more effective aspiration of thrombi, for accommodation of a larger range of medical devices or easier manipulation of medical devices within inner lumen 26, or both.

In the example shown in FIG. 4, substantially no material (e.g., no material or nearly no material) is present between at least some portions of structural support member 20 and at least some portions of outer jacket 24, such that at least a portion of member 20 is in direct contact with outer jacket 24. This direct contact may help distribute flexibility from member 20 to outer jacket 24, which may increase the kink resistance of catheter body 12. In some examples, catheter body 12 is devoid of any material between an outer surface of structural support member 20 (e.g., a coil member) and an inner surface of outer jacket 24, such that the outer surface of member 20 and outer jacket 24 are in direct contact with each other.

In contrast, when a thermoplastic material is used to at least partially fill the spaces defined by structural support member 20 and to mechanically connect member 20 to inner liner 18, the thermoplastic material may melt when outer jacket 24 is heat shrunk onto inner liner 18 and member 20, which may cause structural support member 20 to undesirably migrate relative to inner liner 18, as well as cause the thermoplastic material to reflow and flow between structural support member 20 and outer jacket. While outer jacket 24 may be adhered to member 20 and support layer 22 in order to avoid this reflow, rather than being heat shrunk onto inner liner 18 and member 20, the adhesive may define an additional layer between member 20 and outer jacket 24, which may increase the wall thickness of catheter body 12. Increasing the wall thickness of catheter body 12 in this manner may be undesirable in some cases.

In addition to helping to reduce the thickness T of the wall of catheter body 12, a thermoset polymer may provide better structural integrity to catheter body 12 compared to a thermoplastic polymer. In contrast some or all thermoplastic polymers, a thermoset polymer may include polymers that cross-link together during the curing process. This cross-linking may provide a particular sample of a thermoset polymer with higher temperature resistance, more flexibility, and more dimensional stability compared to a sample of a thermoplastic material having the same dimensions. The higher flexibility and higher dimensional stability may help achieve the desired structural characteristics for catheter body 12, e.g., the desired flexibility, kink-resistance, and pushability. In addition, as discussed above, because a thermoset polymer may be more resistant to high temperatures than a thermoplastic polymer, when support layer 22 is formed from a thermoset polymer, support layer 22 may remain in a cured state (and not reflow) in the presence of high heat, such as during heat shrinking of outer jacket 24 onto support layer 22 and structural support member 20. This may help define structural support member 20 having the structural features, e.g., the desired pitch.

Support layer 22 is configured to fill at least part of the spaces between portions of structural support member 20, e.g., the spaces between turns of structural support member 20 in examples in which member 20 is a coil member. The presence of support layer 22 between turns of member 20 may help distribute the flexibility provided by member 20 along the length of member 20, which may help prevent catheter body 12 from kinking. For example, at least by eliminating voids between turns of structural support member 20, support layer 22 may transfer the flexing motion from structural support member 20 along a length of catheter body 12.

In some examples, support layer 22 has a thickness (measured in a direction orthogonal to longitudinal axis 16) that is greater than or equal to a cross-sectional dimension of the wire that forms the member 20, such that layer 22 is at least partially positioned between outer jacket 24 and structural support member 20.

In other examples, support layer 22 has a thickness that is less than or equal to a cross-sectional dimension of the wire that forms the structural support member 20. In these examples, support layer 22 is not positioned between outer jacket 24 and structural support member 20, such that a thickness T (FIGS. 3 and 4) of the wall of catheter body 12 is smaller compared to examples in which support layer 22 has a thickness that is greater than or equal to a cross-sectional dimension of the wire that forms the member 20.

In the example shown in FIGS. 2-4, structural support member 20 is formed from a wire, such as a rounded (in cross-section) wire, that is shaped to define a helical coil. In other examples, member 20 may be formed, at least in part, from a flat (in cross-section) wire that is shaped to define a helical coil. A rounded wire may define a coil member having a smaller surface area than a flat wire, such that, for a given length of structural support member 20, the rounded wire may be more tightly wound than a flat wire. Because the tightness with which the wire is wound to define the coil member may affect the stiffness of the coil member, the rounded coil member may allow for the formation of a structural support member 20 having a larger range of stiffness than then a flat wire. In this way, a rounded wire may, in some examples, achieve a support member 20 having a more flexible distal portion and a stiffer proximal portion than a flat wire.

The wire from which member 20 is formed can be a metal wire. In some examples, the wire is formed from a shape memory material, such a nickel titanium alloy (Nitinol). In other examples, the wire is formed from stainless steel. In some cases, a nickel titanium alloy may be more crush resistant than stainless steel, and, therefore, may be used to form a structural support member 20 of a catheter that is more resistant to kinking and buckling compared to stainless steel. In addition, as described in further detail below, a shape memory material may allow structural support member 20 to be formed before it is positioned over inner liner 18. For example, the pitch and diameter of member 20 may be defined before member 20 is positioned over inner liner 18, which may provide certain advantages (discussed below). In contrast, when member 20 is formed from stainless steel, the pitch and diameter of member 20 may be defined as member 20 is wound over inner liner 18.

The flexibility of structural support member 20, and, therefore, the flexibility of catheter body 12 may be, at least in part, a function of a pitch of the helical coil defined by structural support member 20. A larger pitch results in larger gaps between adjacent turns of the wire forming member 20 and a higher degree of flexibility. The pitch can be, for example, the width of one complete turn of wire, measured in a direction along longitudinal axis 16.

In some examples, a pitch of structural support member 20 varies along a length of structural support member 20, such that a stiffness (or flexibility) varies along the length. The pitch may continuously vary along the length of member 20, or may progressively change, e.g., include different sections, each section having a respective pitch. An example structural support member 20 that has different sections having different, respective pitches is shown in FIG. 5, which is a side elevation view of a part of structural support member 20.

Figure 5:
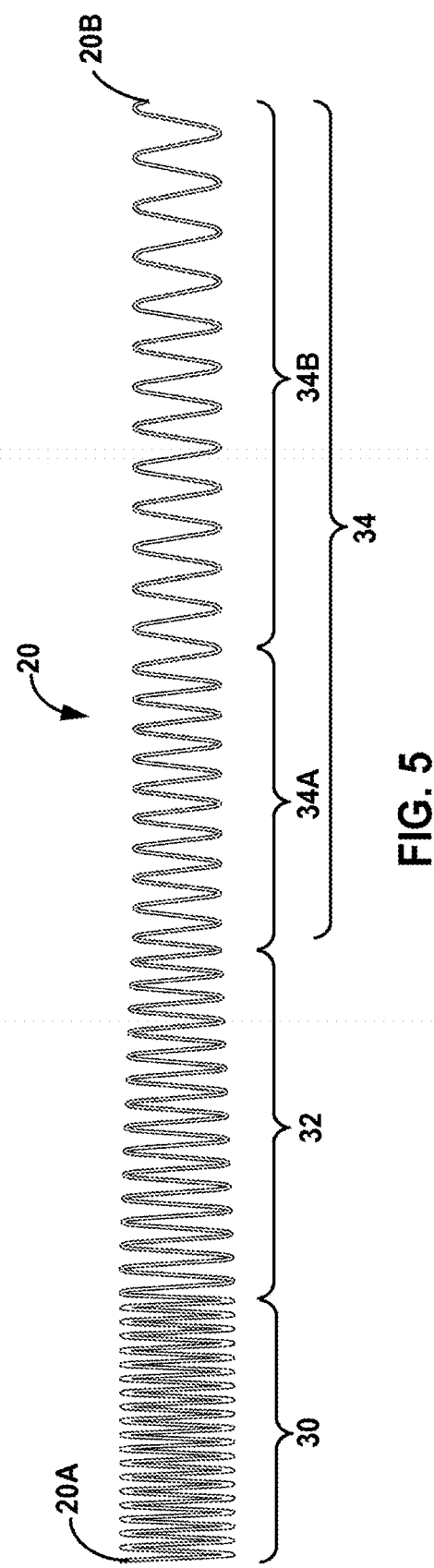
FIG. 5 is a side elevation view of a part of an example structural support member of the catheter body of FIG. 1.

As shown in FIG. 5, a pitch of structural support member 20 decreases in a distal direction, such that proximal portion 30 of member 20 has a greater pitch than medial portion 32, which has a greater pitch than first subportion 34A of distal portion 34, which has a greater pitch than second subportion 34B of distal portion. One or more of the portions 30, 32, 34 of member 20 may have a gradually increasing pitch. Proximal portion 30 may, for example, be positioned within proximal portion 17A (FIG. 1) of catheter body 12, medial portion 32 may be positioned within medial portion 17C of catheter body 12, and distal portion 34 may be positioned within distal portion 17B of catheter body 12.

In one example, proximal portion 30 of member 20 has a pitch of about 0.00225 inches (about 0.057 mm), medial portion 32 has a pitch of about 0.00250 inches (about 0.064 mm), and distal portion 34 includes first subportion 34A having a pitch of about 0.0030 inches (about 0.076 mm) and second subportion 34B having a pitch of that gradually increases from 0.0030 inches to about 0.0070 inches (about 0.18 mm). In some examples, second subportion 34B may have a pitch that increases at a constant rate of change along a length of second subportion 34B. In other examples, second subportion 34B may have a pitch that increases at a varying rate of change along the length.

FIG. 5 is not drawn to scale. In some examples, proximal portion 30 has a length of about 98 cm, medial portion 32 has a length of about 26 cm, and first subportion 34A of distal portion 34 has a length of about 6 cm, and second subportion 34B has a length of about 10 cm. The length of portions 30, 32, 34 may differ in other examples, and may depend on the desired flexibility of catheter body 12.

In some examples, in addition to changing stiffness along the length of structural support member 20, member 20 can change in diameter along a length of member 20. For example, structural support member 20 may taper from a first coil diameter to a second coil diameter. In the example shown in FIG. 5, proximal portion 30 of structural support member 20 has a first coil outer diameter and a first coil inner diameter, distal portion 34 of structural support member 20 has a second coil outer diameter and a second coil inner diameter, and a medial portion 32 of structural support member 20 tapers in outer diameter from the first coil outer diameter to the second coil outer diameter, and tapers in inner diameter from the first coil inner diameter to the second coil inner diameter. Medial portion 32 can, for example, have a length that is substantially the same as medial portion 17C (FIG. 1) of catheter body 12, which tapers from a first outer diameter to a second outer diameter in some examples. For example, medial portion 34 can have a length of about 2 inches. The length of medial portion 32 can be selected to accommodate the desired change in pitch or diameter of member 20 along medial portion 32.

In examples in which inner liner 18 also tapers from a first outer (and/or inner) diameter to a second outer (and/or inner) diameter (smaller than the first outer (and/or inner) diameter), examples in which catheter body 12 tapers from a first outer diameter to a second outer diameter, or both, structural support member 20 may taper to follow the change in the outer diameter of inner liner 18, catheter body 12, or both inner liner 18 and catheter body 12.

In some examples, structural support member 20 is formed from a single wire that defines a coil member that changes in outer diameter and inner diameter, and changes in pitch along the length of member 20. The single wire may be seamless (or joint-less) in that there are no joints (e.g., butt joints) between separate portions of wire that are connected together to define a longer wire. Rather, the wire has a unitary body construction. The contemporaneous change in pitch and inner and outer diameters of the structural support member 20 including a single, seamless wire may be made possible, at least in part, by the shape memory material from which the wire is formed.

Defining member 20 from a single, seamless wire may increase the structural integrity of catheter body 12 compared to examples in which member 20 is formed from multiple wires that are joined together. For example, the joints between wires may adversely affect the tensile strength or lateral flexibility of member 20, which may adversely affect the flexibility and pushability of catheter body 12.

Outer jacket 24 is positioned radially outward of inner liner 18 and structural support member 20, and, in some examples, defines an outer surface of catheter body 12. Although a coating or another material may be applied over the outer surface of outer jacket 24, outer jacket 24 may still substantially define shape and size of the outer surface of catheter body 12. Outer jacket 24, together with structural support member 20 and inner liner 18, may be configured to define catheter body 12 having the desired flexibility, kink resistance, and pushability characteristics.

Outer jacket 24 may have stiffness characteristics that contribute to the desired stiffness profile of catheter body 12. For example, outer jacket 24 may be formed to have a stiffness that decreases from a proximal portion of catheter body 12 to a distal portion. For example, outer jacket 24 may be formed from two or more different materials that enable outer jacket 24 to exhibit the desired stiffness characteristics.

Figure 6:
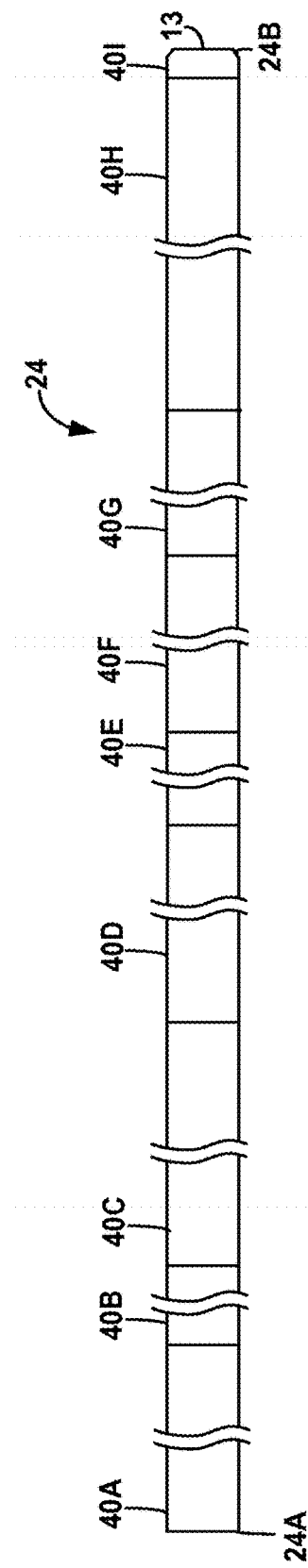
FIG. 6 is a conceptual side elevation view of an example outer jacket that includes a plurality of segments.

FIG. 6 is a conceptual side elevation view of an example outer jacket 24 that includes a plurality of segments 40A-40I (collectively referred to herein as "segments 40" or generally referred to individually as "segment 40"), at least two of the segments 40 having different durometers. The segments 40 can each be, for example, sleeves (e.g., tubular sleeves) that are configured to be positioned over inner liner 18 and structural support member 20, and, if present, support layer 22. At least two segments 40 may also define different inner diameters than each other, where the inner diameter of a particular sleeve 40 may be selected to accommodate the portion of catheter body 12 in which the sleeve 40 is to be positioned. In some examples, each segment 40 has the same wall thickness (measured in a direction orthogonal to longitudinal axis 16 (FIG. 1). In other examples, the wall thicknesses of segments 40 may differ.

Segments 40 are situated longitudinally adjacent to each other, e.g., in an abutting relationship, and can be mechanically connected together to define outer jacket 24 using any suitable technique, such as by welding, an adhesive, or any combination thereof.

The stiffness of outer jacket 24 contributes to the flexibility and structural integrity of catheter body 12. Accordingly, the durometers of each of the segments 40 may be selected to help provide catheter body 12 with the desired flexibility characteristics. For example, in some examples in which catheter body 12 increases in flexibility from proximal end 12A towards distal end 12B, the durometer of each of the outer jacket segments 40 may decrease in a direction from proximal end 24A of outer jacket 24 towards distal end 24B.

In some examples, the durometer of each of the outer jacket segments 40 may decrease in a direction from proximal end 24A of outer jacket 24 towards distal end 24B and then increase proximate to distal end 24B of outer jacket 24. In these examples, outer jacket 24 may define a first section that decreases in durometer along a length of the first section in a direction towards the distal end of the elongated body, and a second section that is more distal than the first section, includes distal end 12B of catheter body 12, and has a higher durometer than a distal-most portion of the first section. As a result of such relative stiffness characteristics, distal opening 13 of catheter body 12 may resist geometric deformation when catheter body 12 is engaged with a guidewire to a greater degree than would occur if the second section were formed of the material of the distal-most portion of the first section.

For example, a durometer of a distal-most outer jacket section 40I may be greater than a durometer than adjacent section 40H. In this example, segments 40A-40H may define the first section of outer jacket 24, and segment 40I may define the second section. As another example, the durometers of outer jacket segments 40H and 40I may be greater than a durometer of outer jacket segment 40G, such that segments 40A-40G define the first section and outer jacket segments 40H and 40I define the second section. In some examples, distal-most segment 40I of outer jacket 24 has a higher durometer, such that it is stiffer, than a segment in the middle of catheter body 12, e.g., one or more of segments 40C-40G.

While it may be desirable in some cases to provide a catheter body 12 having a relatively flexible distal portion, increasing the hardness of a distal-most section of outer jacket 24 relative to a more proximal section that is directly adjacent to the distal-most section, may provide certain advantages in some examples. For example, increasing the hardness of the distal-most section may configure distal opening 13 of catheter body 12 to resist geometric deformation when distal opening 13 (FIG. 1) of catheter body 12 is engaged with a guidewire, which may help support the navigation of catheter body 12 through vasculature. The distal-most section of outer jacket 24 that exhibits the increased stiffness may be a relatively small length of catheter body 12 and, therefore, may not affect the overall flexibility of catheter body 12.

When catheter body 12 is advanced through vasculature of a patient, catheter body 12 may be inserted over a previously placed guidewire, which defines a pathway for catheter body 12 through the vasculature of the patient. Due to the difference in cross-sectional size of catheter body 12 and the guidewire, the guidewire may not substantially fully (e.g., completely or nearly completely) occupy the space within inner lumen 26. As a result, when the guidewire is not centered within inner lumen 26, only one side of catheter body 12 may engage with the guidewire, e.g., as catheter body 12 is guided over the guidewire along a curvature. The guidewire may cause a radially outward force to be applied to the wall of catheter body 12. The hardness of the distal-most portion of outer jacket 24 is selected to help distal tip of catheter body 12 resist ovalization or other geometric deformation in such circumstances, e.g., when the wall of the catheter body 12 is engaged with a guidewire. Ovalization or other geometric deformation of catheter body 12 may cause the shape of distal opening 13 of catheter body 12 to change shape, which may be undesirable in some situations, as it may adversely affect the navigability of the catheter body through the vasculature.

As discussed in further detail below with respect to FIG. 7, in some examples, structural support member 20 does not extend all the way to distal end 12B of catheter body 12, but, rather, ends at a point that is proximal to the distal end 12B. For example, structural support member 20 may end about 0.25 mm to about 1 mm, such as about 0.5 mm, from distal end 12B. Thus, structural support member 20 may not contribute to the structural integrity of a distal-most portion of catheter body 12. Extending structural support member 20 to the distal end 12B of catheter body 12 may limit the flexibility of the distal-most portion. By configuring outer jacket 24 to include a second section that has a higher durometer than a distal-most portion of the first section, the distal tip of catheter body 12 may exhibit a stiffness that is sufficient to facilitate a distal opening 13 that is resists geometric deformation, but is also flexible enough to guide catheter 12 through tortuous vasculature. In this way, increasing the stiffness of outer jacket 24 at a distal tip of catheter body 12 may help maintain desired navigability of catheter body 12, even without the presence of structural support member 20 in the distal tip.

In some cases, catheter body 12 is advanced over an inner catheter having a smaller outer diameter than catheter body 12, rather than directly over a guidewire. The inner catheter may, for example, help fill the space between the guidewire and the outer surface of outer catheter body 12 in order to help minimize the ledge effect, which may occur when a distal tip of catheter body 12, particularly the portion of the edge of the tip that tracks the outside of a curve formed by the body 12, engages with or abrades a wall of vasculature as catheter body 12 is advanced over a guidewire through a curve in the vasculature. The ledge effect may, at least in part, be attributable to unopposed space between the guidewire and inner lumen 26 of catheter body 12. In some examples, configuring a distal tip of catheter body 12 to define opening 13 configured to resist geometric deformation may allow catheter body 12 to be guided through vasculature over a guidewire, without need for an inner catheter. This may not only reduce costs associated with the medical procedure, but may also reduce the time required to reach the target tissue site as a step of guiding the inner catheter to the tissue site before guiding catheter 10 to the target tissue site may be eliminated.

In examples in which catheter 10 is used for aspiration, in addition to, or instead of, being selected to configure the distal tip of catheter body 12 to resist geometric deformation when catheter body 12 is advanced over a guidewire, the hardness of the second section of outer jacket 24 may be selected to help distal opening 13 of catheter body 12 resist geometric deformation during aspiration. For example, at least outer jacket segment 40I, which together with inner liner 18, defines distal opening 13, may have a stiffness that allows opening 13 to substantially hold its shape and not collapse inward towards or into inner lumen 26 when the vacuum force is applied to inner lumen 26.

Outer jacket segments 40 may each be formed from the same material or at least two segments 40 may be formed from different materials. Example materials for segments 40 include, but are not limited to, polymers, such as a polyether block amide (e.g., PEBAX®, commercially available from Arkema Group of Colombes, France), an aliphatic polyamide (e.g., Grilamid®, commercially available from EMS-Chemie of Sumter, S.C.), another thermoplastic elastomer or other thermoplastic material, or combinations thereof. In one example, segment 40A is formed from an aliphatic polyamide and segments 40B-40I are formed from a polyether block amide. The compositions of the polyether block amide may be modified to achieve segments 40 having different durometers.

In some examples, segment 40A has a durometer greater than or equal to about 72D, segment 40B has a durometer greater than or equal to about 72D and less than or equal to the durometer of segment 40A, segment 40C has a durometer of about 72D, segment 40D has a durometer of about 63D, segment 40E has a durometer of about 55D, segment 40F has a durometer of about 40D, segment 40G has a durometer of about 35D, segment 40H has a durometer of about 25D, and segment 40I has a durometer greater than about 25D, such as a about 55D. In other examples, however, one or more of the segments 40 may have other hardness values. The hardness of the segments 40 may be selected to obtain more or less flexibility, torqueability, and pushability for all or part of catheter body 12.

Segments 40 may each have any suitable length, which may be selected based on the desired flexibility profile of catheter body 12. In some examples, proximal, distal, and medial portions 17A-17C (FIG. 1) of catheter body 12 may have their own respective outer jacket segments 40 that each begin and end at the proximal and distal ends of the corresponding catheter body portion 17A-17C. In other examples, one of the outer jacket segments 40 may extend at least over both proximal portion 17A and tapering medial portion 17C, and/or over both medial portion 17C and distal portion 17B.

Figure 7:
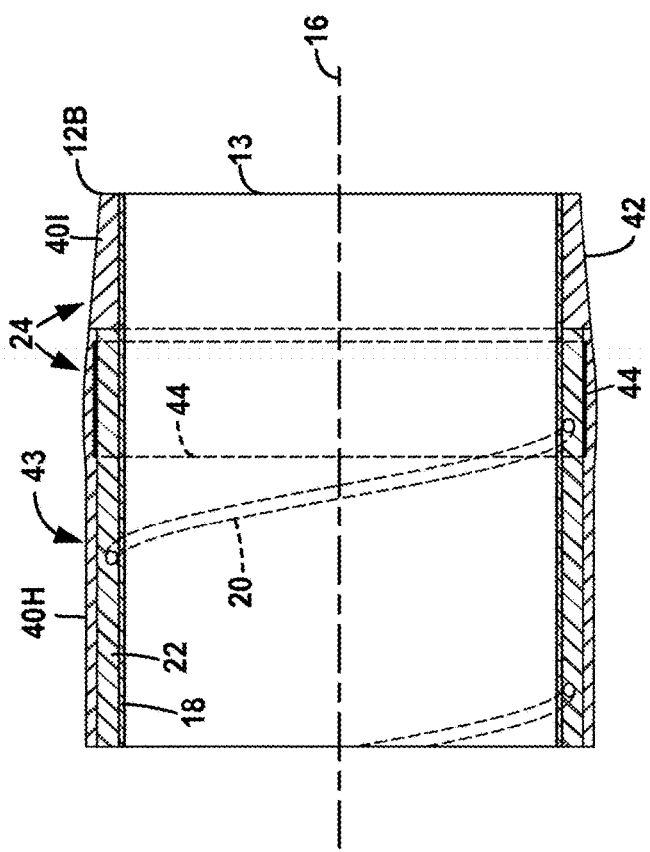
FIG. 7 is a conceptual cross-sectional view of an example distal-most portion of the catheter body of FIG. 1, which includes the distal tip of the catheter body.

FIG. 7 is a conceptual cross-sectional view of an example distal-most portion of catheter body 12, which includes the distal tip of catheter body 12. Distal opening 13 is located at the distal tip. In some examples, the distal tip is defined by the portion of catheter body 12 including distal-most segment 40I of outer jacket 24. In other examples, the distal tip may include additional sections of outer jacket 24.

As shown in FIG. 7, inner liner 18 and outer jacket 24 extend to distal end 12B of catheter body 12, whereas structural support member 20 and support layer 22 both terminate at a location that is proximal to distal end 12B. In the example shown in FIG. 7, structural support member 20 and support layer 22 are at least partially coextensive (e.g., extend over a common space) with at least a medial portion of inner liner 18 and outer jacket 24 (e.g., segments 40B-40H, or only a portion of segments 40B-40H), but not with the portions of inner liner 18 and outer jacket 24 at the distal tip of catheter body 12. Thus, in the example shown in FIG. 7, distal opening 13 of catheter body 12 is defined by inner liner 18 and outer jacket 24, but not by structural support member 20 and support layer 22. In these examples, the distal tip of catheter body 12 may consist essentially of inner liner 18 and outer jacket 24. While the distal tip may also include adhesive or the like between inner liner 18 and outer jacket 24, a coating on outer jacket 24, or other layers, the structural characteristics of the distal tip of catheter body 12 may be primarily influenced by only inner liner 18 and outer jacket 24.

A distal tip that consists essentially of only inner liner 18 and outer jacket segment 24 may define a relatively thin-walled distal tip, which may allow for a greater inner diameter to outer diameter ratio at the distal tip. A larger inner diameter to outer diameter ratio may be useful for aspiration, target (e.g., thrombus) capture, as well as maneuvering devices within inner lumen 26, such that the increasing the inner diameter to outer diameter ratio may be desirable.

In the example shown in FIG. 7, structural support member 20 and support layer 22 both terminate in a region of outer jacket 24 that has a lower durometer than distal-most segment 40I of outer jacket 24. In other examples, however, one or both of structural support element 22 and support layer 22 may terminate in a portion of catheter body 12 that includes outer jacket segment 40I, such that one or both of structural support member 20 and support layer 22 overlap with distal-most outer jacket segment 40I.

When distal end 12B of catheter body 12 is introduced into vasculature of a patient, distal end 12B of catheter body 12 leads catheter 10 through the vasculature. As a result, it may be desirable for distal end 12B of catheter body 12 to define an atraumatic tip, such that as catheter body 12 is navigated through curves in the vasculature, distal end 12B provides a relatively smooth and atraumatic interface with the walls of vasculature ("vascular walls"). In the example shown in FIG. 7, the distal tip of catheter body 12 is configured to be relatively atraumatic when it engages with tissue (e.g., vascular walls) of the patient, yet stiff enough to allow at least distal opening 13 to substantially maintain its cross-sectional shape or otherwise resist geometric deformation as the distal tip is maneuvered over a guidewire or another device (e.g., another catheter). For example, outer jacket segment 40I may define an outer surface 42 that tapers from a larger outer diameter to a smaller outer diameter at distal end 12A of catheter body 12. The angled outer surface 42 (angled relative to the longitudinal outer surface 43 of catheter body 12) may help guide the distal tip of catheter body 12 along a curved vascular wall, and may help reduce adverse interactions between the distal tip of catheter body 12 and the vascular wall.

Because the distal tip of the example of catheter body 12 shown in FIG. 7 is devoid of structural support member 20 and support layer 22, a thickness of outer jacket 24 may be increased in some examples to accommodate angled outer surface 42 without requiring a corresponding increase the outer diameter of catheter body 12. For example, outer jacket segment 40I may be thicker than outer jacket segment 40H (the thickness being measured in a direction orthogonal to longitudinal axis 16), but the outer surfaces of outer jacket segments 40H, 40I may be substantially continuous.

Distal-most segment 40I of outer jacket 24 at distal end 12B of catheter body 12 can be formed of any suitable material. For example, segment 40I may be formed of a polyether block amide (e.g., PEBAX), which is relatively stiff and may allow the distal tip of catheter body 12, and, therefore, distal opening 13, to substantially maintain its shape and resist geometric deformation as it is guided through vasculature over a guidewire or another device.

In some examples, catheter body 12 includes radiopaque marker 44, which may be attached to inner liner 18, support layer 22, and/or outer jacket 24 using any suitable technique. In some examples, outer jacket 24 is positioned over marker 44, which may help prevent an outer surface of marker 44 from being exposed. In the example shown in FIG. 7, radiopaque marker 44 is at least partially embedded in support layer 22 (e.g., fully embedded or partially embedded along its longitudinal length) and adhered to inner liner 18 via support layer 22. In other examples, radiopaque marker 44 may be attached to inner liner 18 via outer jacket 24, which, when heat shrunk over member 20 and inner liner 18, or otherwise secured to member 20 and inner liner 18, may substantially fix marker 44 in place. Radiopaque marker 44 may be formed from any suitable material, and may be in the form of a continuous ring, a discontinuous ring, or multiple segments that extend around the perimeter of catheter body 12. Radiopaque marker 44 may be positioned to indicate the location of the distal tip of catheter body 12 and, therefore, may be positioned proximate to distal opening 13.

In the example shown in FIG. 7, the portion of catheter body 12 that is distal to radiopaque marker 44 may consist essentially of inner liner 18 and outer jacket 18, which may be advantageous for at least the reasons discussed above. In other examples, the portion of catheter body 12 that is distal to radiopaque marker 44 may also include other structures, such as, but not limited to, structural support member 20 and support layer 22.

Although FIG. 7 illustrates catheter body 12 including structural support member 20 that includes a coil, in other examples, the features described with respect to FIG. 7 and the other features described herein may be used with other types of structural support members 20. For example, rather than structural support member 20 in the form of a coil, in other examples of catheter body 12 having a distal tip defined by outer jacket segment 40I and inner liner 18, and devoid of structural support member 20, member 20 may include a braided structure that is attached to inner liner 18, a cut or uncut hypotube that overlies inner liner 18, or any combination thereof.

In addition, although FIG. 7 is described with respect to catheter body 12, in other examples, one or more features of the distal tip configuration shown in FIG. 7 may be used with catheter bodies having other configurations such as catheter bodies having substantially constant outer diameters, catheter bodies that include an inner liner formed from multiple inner liner sections connected together, catheter bodies that include a structural support member that includes one or more sections mechanically connected together or a structural support member that does not have a varying pitch and/or a varying diameter, catheter bodies that include one or more layers of material between an outer surface of structural support member 20 and outer jacket 24, or any combination thereof.

Figure 8:
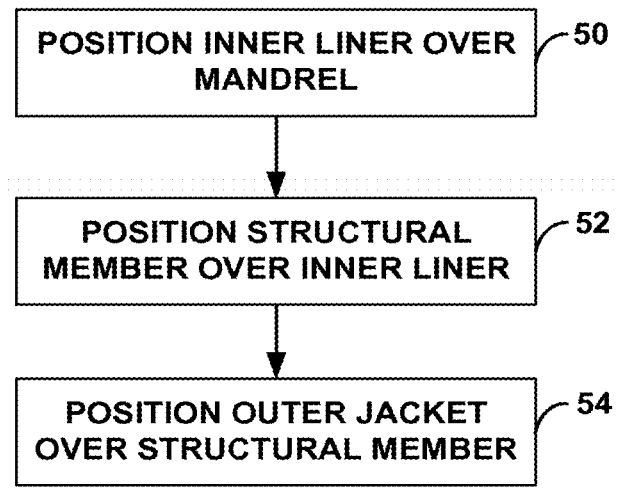
FIGS. 8 and 9 are flow diagrams of example methods of forming the catheter of FIG. 1.
Figure 9:
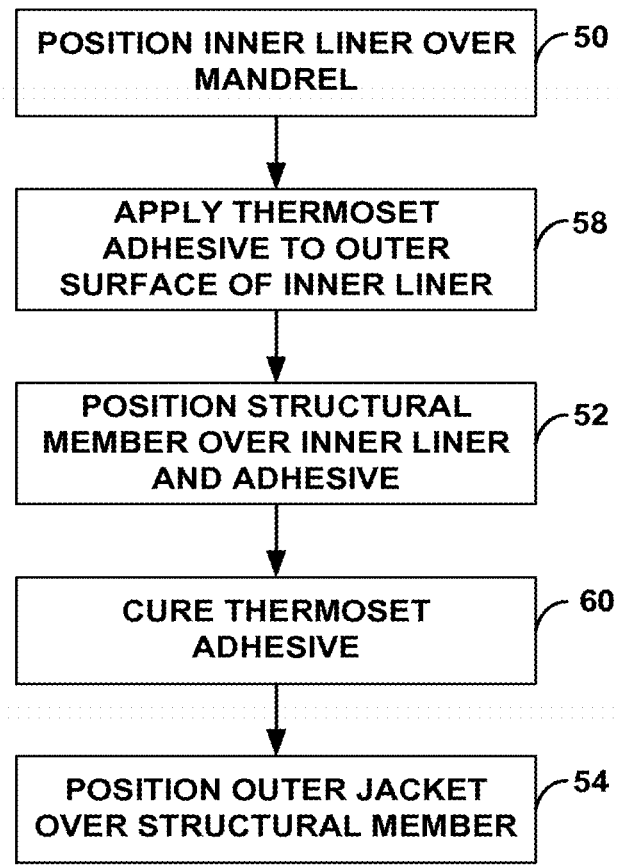

The catheters described herein can be formed using any suitable technique. FIGS. 8 and 9 are flow diagrams of example methods of forming catheter 10, and are described with reference to FIGS. 10 and 11, which are schematic side elevation views of assemblies after some steps of the methods. In accordance with the technique shown in FIG. 8, inner liner 18 may be positioned over mandrel 48 (50). In some examples, inner liner 18 is a unitary, seamless body, and may be positioned over mandrel 48 by at least inserting mandrel 48 through an end of inner liner 18.

Figure 10:
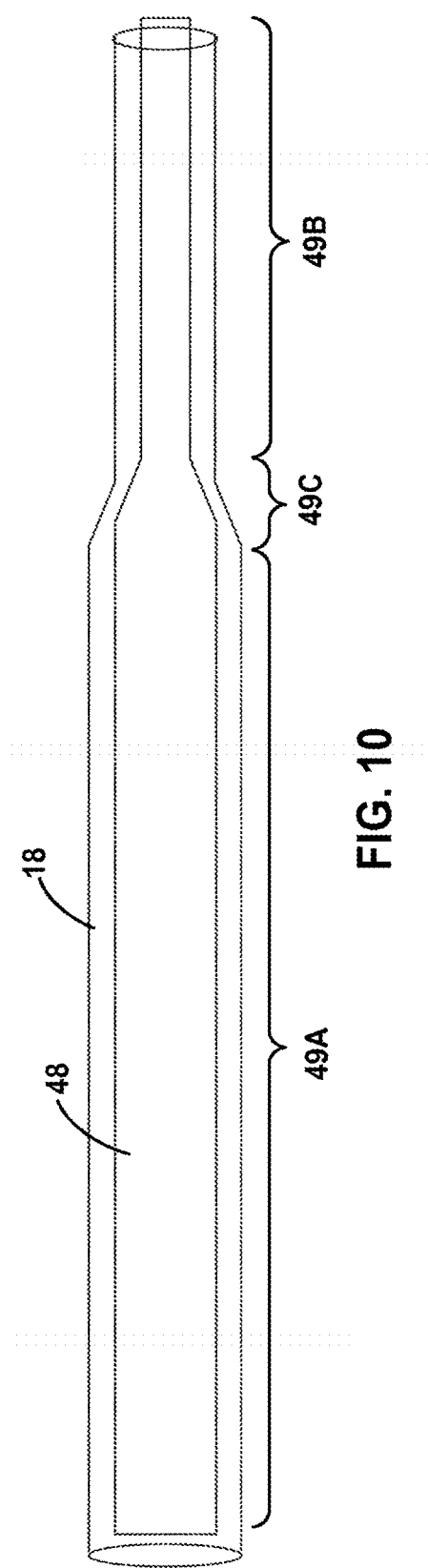
FIG. 10 is a schematic side elevation view of a mandrel and an inner liner positioned over the mandrel.

As discussed above, in some examples, catheter body 12 tapers from proximal portion 17A (FIG. 1) having a first, constant outer diameter to distal portion 17B having a second, constant outer diameter, e.g., along medial portion 17C, which continuously tapers from the first outer diameter to the second outer diameter. Mandrel 48 defines a corresponding change in outer diameter. For example, as shown in FIG. 10, mandrel 48 includes proximal portion 49A having a first mandrel outer diameter that is substantially constant (e.g., constant or nearly constant, except for minor manufacturing variances) along proximal portion 49A, distal portion 49B having a second mandrel outer diameter that is substantially constant along distal portion 49B, and medial portion 49C, which continuously tapers from the first mandrel outer diameter to the second mandrel outer diameter.

The length (measured in a direction parallel to a longitudinal axis of mandrel 48) of each of portion 49A-49C may be selected based on the desired length of proximal, distal, and medial portions 17A-17C, respectively, of catheter body 12. For example, medial portion 49C may have a length of about length of about 1 inch (about 2.5 cm) to about 3 inches (about 7.6 cm), such as about 2 inches (about 5 cm).

Mandrel 48 may be formed from any suitable material. The material from which mandrel 48 is formed may be configured to relatively easily release inner liner 18, e.g., after catheter body 12 is formed over mandrel 48. For example, mandrel 48 may be formed from an extruded PTFE (e.g., mandrel 48 may consist of or consist essentially of an extruded PTFE). An extruded PTFE material may define a relatively lubricious outer surface, which may allow for relatively easy release of inner liner 18 from mandrel 48, e.g., even in the absence of one or more additional lubricious coatings on the outer surface of mandrel 48. In addition, an extruded PTFE material may be ground or otherwise shaped to define mandrel 48 having the desired portion 49A-49C. Medial portion 49C, which continuously tapers in outer diameter may be relatively difficult to define with some materials. However, an extruded PTFE bead, which may be a solid, unitary rod, may be relatively easily manipulated (e.g., by grinding) to achieve the desired geometry to provide medial portion 49C.

In some examples, in the technique shown in FIG. 8, after positioning inner liner 18 over mandrel 48, inner liner 18 may be heat shrunk onto mandrel 48 and may, as a result, conform to the outer surface of mandrel 48 and acquire the tapered profile of mandrel 48. For example, inner liner 18 may have a somewhat larger inner diameter than mandrel 48 in order to permit inner liner 18 to be relatively easily slipped over one end of mandrel 48. In other examples, however, heat shrinking may not be necessary. For example, in addition to, or instead of, heat shrinking, inner liner 18 may be longitudinally stretched over mandrel 48 in order to substantially conform to the outer surface of mandrel 48. In either example, inner liner 18 may define a constant inner diameter or may have different inner diameters, e.g., corresponding to the outer diameters defined by mandrel 48.

Using a single PTFE bead that is ground or otherwise shaped to define mandrel 48 may help reduce surface protrusions or other irregularities that may transfer from outer surface of mandrel 48 to the inner surface of inner liner 18. Surface protrusions or other irregularities along the inner surface of inner liner 18 may interfere with the passage of devices within inner lumen 26 of catheter body 12. Thus, a smoother inner surface of inner liner 18 may be desirable in some cases, e.g., in order to allow a clinician to guide catheter body 12 over a guidewire with relative ease, or to introduce another medical device through inner lumen 26.

In other examples, multiple extruded PTFE portions may be attached end-to-end to define mandrel 48. For example, PTFE portions corresponding to portions 49A-49C may be adhered or welded to define butt joints that are axially separated along a length of mandrel 48. However, attaching multiple PTFE portions to define mandrel 48 may introduce more surface protrusions or other irregularities along the inner diameter of inner liner 18 compared to examples in which a single PTFE bead is used to form mandrel 48. For example, the joints between the PTFE portions may cause surface protrusions to form along the inner surface of inner liner 18 when inner liner 18 is positioned over mandrel 48 and substantially conforms to the outer surface of mandrel 48.

Because mandrel 48 defines an outer diameter that changes over a length of mandrel 48, when inner liner 18 is positioned over mandrel 48 and substantially conforms to an outer surface of mandrel 18, inner liner 18 may be acquire the profile of mandrel 48. Thus, mandrel 48 helps to define inner liner 18 that includes a proximal inner lumen portion having a first inner lumen diameter, a distal inner lumen portion having a second inner lumen diameter, and a medial inner lumen portion that gradually tapers in diameter from the first inner lumen diameter to the second inner lumen diameter.

Figure 11:
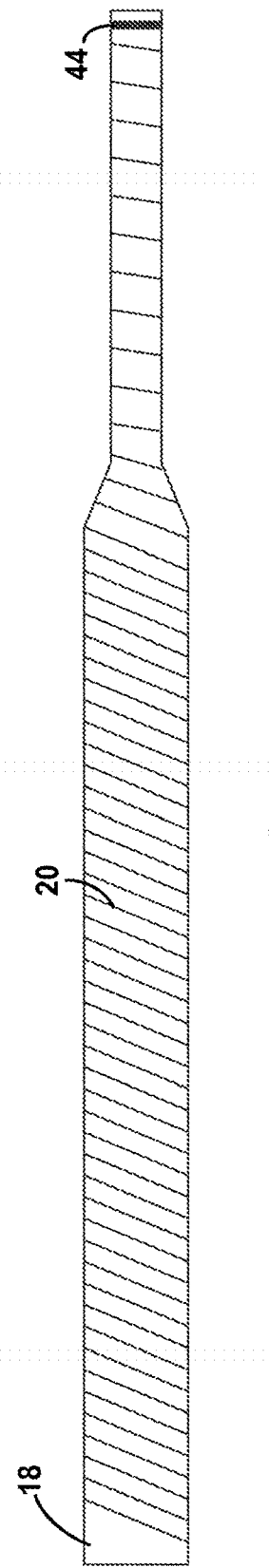
FIG. 11 is a schematic side elevation view of an example structural support member positioned over an inner liner.

After positioning inner liner 18 over mandrel 48 (50), structural support member 20 may be positioned over inner liner 18, as shown in FIG. 11 (52). In examples in which structural support member 20 includes a coil member, the wire defining the coil member may be wound over an outer surface of inner liner 18 or pushed over inner liner 18. The coil member can be, for example, a single coil member that is devoid of any joints. In some examples, the structural configuration of structural support member 20 may be at least partially defined prior to being positioned over inner liner 18. For example, a shape memory wire (e.g., a nickel-titanium wire) or a wire of an otherwise heat-settable metal or alloy may be wound over a different mandrel (e.g., a "coil mandrel") on which inner liner 18 is not present or over mandrel 48 (e.g., before inner liner 18 is positioned on mandrel 48) to define at least one of the desired coil pitch, the desired coil diameter, the desired tapering profile (e.g., a continuous tapering or progressive tapering), or the desired length of structural support member 20, and then heat set to substantially hold its shape. The wire may then be subsequently unwound from the mandrel onto a reel or a bobbin, and then positioned over inner liner 18. Structural support member 20 may be positioned over inner liner 18 by, for example, winding member 20 over inner liner 18 (e.g., winding member 20 from the bobbin or reel onto inner liner 18) or by pushing inner member 20 over an end of inner liner 18.

In some examples, a wire formed from a shape memory metal/alloy or an otherwise heat-settable metal/alloy may be preformed into a helical coil having a constant pitch and the desired diameters, including the desired taper, and then, once positioned over inner liner 18, the layout of the coiled wire may be adjusted to achieve the desired pitch profile (e.g., the change in pitch over the length) of structural support member 20. For example, the pitch of the wire may be adjusted over inner liner 18 to achieve the desired pitch profile (e.g., as described with reference to FIG. 5). These adjustments may be made manually, by hand, or by a computer-controlled device. In other examples, however, a wire may be preformed into a helical coil having the desired pitch profile and diameters for structural support member 20 before being positioned over inner liner 18.

Defining some or all of the structural characteristics of structural support member 20 prior to positioning member 20 over inner liner 18 may help control the structural characteristics of structural support member 20, as well as control the uniformity of the structural support member 20 of multiple catheter bodies. Pre-shaping and shape-setting the member 20 as a coil (as opposed to ordinary wire stock) causes the member 20 to conform closely to the inner liner 18 as the member 20 is wound onto the liner 18. This close conformance, on its own and in combination with the resulting reduced need for adhesives or other measures to keep the wound member in place on the liner 18, helps reduce the wall thickness T in the catheter body 12. In addition, shape-setting the structural support member 20 on a separate, heat-resistant mandrel enables the construction of the catheter body 12 using the member 20 on a mandrel made of PTFE or other lubricious, non-heat resistant material.

In some examples, the structural configuration of structural support member 20 may be at least partially defined as it is wound over inner liner 18 in some examples. For examples, a shape memory wire or a stainless steel wire may be wound over inner liner 18 to define the desired coil pitch, the desired diameter(s), the desired taper, the desired length, or any combination thereof of member 20. The shape memory wire may then be heat set to define structural support member 20.

Structural support member 20 may be secured in place relative to inner liner 18 using any suitable technique. For example, member 20 may be adhered to inner liner 18. In some examples, an adhesive and/or a polymer is applied over member 20 after member 20 is positioned over inner liner 18. In other examples, as described with reference to FIG. 9, an adhesive may be positioned over inner liner 18 prior to positioning structural support member 20 over inner liner 18. In addition to, or instead of, an adhesive, outer jacket 24 may be used to secure structural support member 20 to inner liner 18.

In the technique shown in FIG. 8, after structural support member 20 is positioned over inner liner (52), outer jacket 24 is positioned over an outer surface of structural support member (54). In some examples, outer jacket 24 is adhered to an outer surface of structural support member 20, e.g., an adhesive and/or a polymer may be applied to outer surface of member 20 prior to positioning outer jacket 24 over member 20 and then cured after outer jacket 24 is positioned over member 20. In addition to, or instead of, the adhesive, outer jacket 24 may be heat shrunk over member 20 and inner liner 18. In some examples, the heat shrinking of outer jacket 24 helps secure member 20 in place relative to inner liner 18.

As noted above, in some examples, catheter body 12 includes support layer 22. In the method shown in FIG. 9, in order to form support layer 22, a layer of thermoset polymer is applied to an outer surface of inner liner 18 after inner liner 18 is positioned over mandrel 48 but before structural support member 20 is positioned over inner liner 18 (58). The thermoset polymer may be, for example, a viscoelastic thermoset polyurethane (e.g., Flexobond 430).

Structural support member 20 may then be positioned over inner liner 18 and the thermoset polymer (52). At least some of the thermoset polymer may be displaced by member 20 when member 20 is positioned over inner liner 18, which may cause at least some of the thermoset polymer to be positioned between the turns of the wire defining member 20. Positioning the thermoset polymer over inner liner 18 prior to positioning member 20 over inner liner 18 in this manner may help minimize or event eliminate air pockets that may form in support layer 22. For example, the force applied by member 20 (in a direction towards inner liner 18) that causes the thermoset polymer to be displaced may also help positively displace any air that may be positioned between member 20 and the thermoset polymer. In contrast, depositing a polymer over member 20 and inner liner 18 may create air pockets between member 20 and the polymer. Air pockets may contribute to the tendency of catheter body 12 to kink.

In addition, by applying the layer of thermoset polymer material over the outer surface of inner liner 18 before positioning structural support member 20 over inner liner 18, the thermoset polymer may be positioned between inner liner 18 and member 20. In contrast, if the thermoset polymer is applied over member 20 after member 20 is positioned over inner liner 18, the thermoset polymer may not be positioned between inner liner 18 and member 20, which may reduce the structural integrity of catheter body 12.

In some examples, in order to help minimize the wall thickness of catheter body 12, substantially no part of support layer 22 (e.g., no support layer material or nearly no support layer material) may be positioned between member 20 and outer jacket 24. Thus, to minimize or even eliminate adhesive from extending radially outwards of structural support member 20, the thermoset polymer may be applied in a relatively thin layer, e.g., in a layer having a thickness less than a thickness of member 20 measured in a direction radially outward from inner liner 18.

As discussed above, structural support member 20 may be at least partially preformed into a helical coil before being positioned over inner liner 18 and the thermoset polymer. The thermoset polymer may be configured to be time cured and/or heat cured, such that the adhesive may not substantially immediately fix the position of member 20 relative to inner liner 18. As a result, in some examples, the pitch of the coil (e.g., along the medial portion 32 (FIG. 5)) may be adjusted after member 20 is positioned over inner liner 18 and the thermoset polymer.

In accordance with the technique shown in FIG. 9, after structural support member 20 is positioned over inner liner 18 and the thermoset polymer (52), the thermoset polymer is cured (60), e.g., by heating and/or time-curing. The cured thermoset polymer defines support layer 22. In some examples, such as some examples in which the thermoset polymer is a thermoset polyurethane, the subassembly including mandrel 48, inner liner 18, the thermoset polymer, and structural support member 20 may be heat cured, e.g., at a temperature of about 200 degrees Fahrenheit (° F.) (about 93.33 degrees Celsius (° C.)) for about two hours.

After the thermoset polymer is cured, outer jacket 24 may be positioned over the outer surface of structural support member 20 and over portions of support layer 22 that are n not covered by structural support member 20 (54). For example, if outer jacket 24 comprises a plurality of different segments 40 (FIG. 6), at least some of the segments 40 may be slid over the outer surface of member 20. The segments 40 may be mechanically connected together and configured to substantially conform to the outer surface of support layer 22 and member 20 using any suitable technique. In some examples, segments 40 are formed from a heat shrinkable material. A heat shrink tube may be positioned over segments 40, and heat may be applied to cause the heat shrink tube to wrap tightly around segments 40. The heat and wrapping force may cause segments 40 to fuse together to define a substantially continuous outer jacket 24. The heat shrunk tube may then be removed from the assembly, e.g., via skiving or any suitable technique.

The use of heat shrinking to apply outer jacket 24 to the subassembly including inner liner 18, support layer 22, and structural support member 20 may help eliminate the need for an adhesive between structural support member 20 and outer jacket 24. This may help minimize the wall thickness of catheter body 12 and, therefore, increase the inner diameter of catheter body 12 for a given outer diameter. In addition, the absence of an adhesive layer adhering support layer 22 and structural support member 20 to outer jacket 24 may contribute to an increased flexibility of catheter body 22.

In some examples, all of the outer jacket segments 40 are attached to the subassembly including inner liner 18, support layer 22, and structural support member 20 in this manner. In other examples, all of the outer jacket segments 40 except for the one or more segments 40 at the distal tip of catheter body 12 are attached to the subassembly including inner liner 18, support layer 22, and structural support member 20 in this manner. In this example, after the heat shrink tubing is removed, the one or more segments 40 (e.g., segment 40I) selected to be at the distal tip of catheter body 12 may be positioned over the distal end of inner liner 18 and welded or otherwise mechanically connected to the distal-most outer jacket segment 40 (e.g., segment 40H) that is already attached to the subassembly. In this way, distal tip at distal end 12B of catheter body 12 may be formed to include inner liner 18 and outer jacket 24, but may be substantially devoid (devoid or nearly devoid) of support layer 22 and structural support member 20.

In addition, in examples in which catheter body 12 includes radiopaque marker 44, marker 44 may be positioned over inner liner 18, as shown in FIG. 11, before positioning outer jacket segments 40 over member 20, or at least before positioning the distal outer jacket segments 40 over member 20. In addition, hub 14 can be attached to proximal end 14A of catheter body 12 using any suitable technique, such as an adhesive, welding, or any combination thereof.

A thermoset polymer may be configured to substantially retain its cured state (and not reflow), even in the presence of the heat that is applied during the heat shrinking of outer jacket segments 40 onto support layer 22 and structural support member 20. For example, the melting temperature of the thermoset polymer defining support layer 22 may be greater than the temperature to which support layer 22 is subjected during the heat shrinking of outer jacket segments 40 onto support layer 22 and structural support member 20. Thus, support layer 22 including a thermoset polymer may substantially fix the position of structural support member 20 relative to inner liner 18 during the placement of outer jacket 24 over support layer 22 and member 20. A support layer 22 that is configured to prevent structural support member 20 from shifting relative to inner liner 18 during the placement of outer jacket 24 over support layer 22 and member 20 in this manner may help control the structural integrity of catheter body 12.

In addition, a thermoset polymer that is configured to substantially retain its cured state during the placement of outer jacket 24 may help minimize or even prevent the material forming support layer 22 from reflowing into the space between outer jacket 24 and structural support member 20. As discussed above, minimizing or event eliminating the presence of support layer 22 material between member 20 and outer jacket 24 may help minimize the wall thickness of catheter body 12 and, therefore, increase the inner diameter of catheter body 12 for a given outer diameter.

In some examples, catheter 10 or catheter body 12 may be a part of an assembly that includes, e.g., a guidewire and/or another catheter. The catheter 10 or catheter body 12 in such an assembly can be any of the embodiments or examples of the catheter 10 or catheter body 12 disclosed herein. The guidewire may be used to guide catheter 10 to a target tissue site within the vasculature of a patient. In addition, in some examples, the additional catheter of the assembly may also be configured to guide catheter 10 or body 12 to a target tissue site within the vasculature of a patient. The additional catheter of the assembly may be substantially similar (e.g. identical or nearly identical) in construction to catheter 10 (including any of the embodiments or examples of the catheter 10 disclosed herein), but may have proportionally greater or smaller dimensions, such that the catheter bodies of the catheters may nest together. For example, the additional catheter of the assembly may have a smaller outer diameter than catheter body 12 and may be placed and/or guided over the guidewire, and then catheter 10 or catheter body 12 may be guided over the additional catheter. If, for example, catheter 10 or body 12 tapers from a 6 French outer diameter to a 5 French outer diameter, then the additional catheter may taper from a 4 French outer diameter to a 3 French outer diameter. The assembly may therefore comprise the catheter 10 with the additional catheter positioned in the inner lumen 26 of the catheter, and may further comprise the guidewire positioned in the inner lumen of the additional catheter.

Each of the components of the assembly may be slidably disposed relative to the other(s) so that each may be advanced and/or retracted over or within the other(s). For example, when the additional catheter is positioned in the lumen of the catheter 10, the catheter 10 may be advanced or retracted longitudinally over the additional catheter, and/or the additional catheter can be advanced or retracted longitudinally within the catheter 10. The use of the additional catheter in this manner may help reduce any adverse interactions with tissue attributable to the ledge effect. For example, if in use of an assembly having a guidewire the guidewire is first advanced into the vasculature, the additional catheter may next be advanced over the guidewire before the catheter 10 is advanced over the additional catheter. The difference in outer diameter between the guidewire and the additional catheter (and between the additional catheter and the catheter 10) is less than the difference in outer diameter between the guidewire and the catheter 10. Therefore, any ledge effect arising from advancing the catheter 10 over a "bare" guidewire may be mitigating by use of the additional catheter in this manner. In other examples, the additional catheter of the assembly may have a larger outer diameter than catheter 10 or body 12 and may be guided over catheter 10 or body 12 to a target tissue site within the vasculature of the patient. If, for example, catheter 10 or body 12 tapers from a 4 French outer diameter to a 3 French outer diameter, then the additional catheter may taper from a 6 French outer diameter to a 4 French outer diameter.

In some examples, a method of using catheter 10 comprises introducing a guidewire or an inner catheter into vasculature (e.g., an intracranial blood vessel) of a patient via an access point (e.g., a femoral artery), and guiding catheter body 12 over the guidewire or the inner catheter. In examples in which outer jacket 24 of catheter body 12 increases in stiffness at the distal tip of catheter body 12, e.g., as discussed with respect to FIGS. 6 and 7, distal opening 13 may resist geometric deformation, even as it engages with the guidewire. For example, when introducing the guidewire into the vasculature, a curve may be formed in the guidewire. Catheter body 12 may be advanced catheter over the curve in the guidewire and the distal opening of the catheter may resist geometric deformation when the catheter is advanced over the curve to a greater degree than would occur if the second section were formed of the material of the distal portion of the first section.

Once distal end 12B of catheter body 12 is positioned at the target tissue site, which may be proximal to thromboembolic material (e.g., a thrombus), the thromboembolic material be removed from the vasculature via catheter body 12. For example, the thromboembolic material may be aspirated from the vasculature by at least applying a vacuum force to inner lumen 24 of catheter body 12 via hub 14 (and/or proximal end 12A), which may cause the thromboembolic material to be introduced into inner lumen 24 via distal opening 13. Optionally, the vacuum or aspiration can be continued to thereby draw the thromboembolic material proximally along the inner lumen 24, all or part of the way to the proximal end 12A or hub 14. As a further option, the aspiration or vacuum may cause the thromboembolic material to attach or adhere to the distal tip; in such a case the catheter 10 or catheter body 12 and the thromboembolic material can be withdrawn from the vasculature together as a unit, for example through another catheter that surrounds the catheter 10 or catheter body 12. In examples in which outer jacket 24 of catheter body 12 increases in stiffness at the distal tip of catheter body 12, e.g., as discussed with respect to FIGS. 6 and 7, distal opening 13 may resist geometric deformation during the aspiration. As another example, the thromboembolic material may be removed from the vasculature using another technique, such as via an endovascular retrieval device delivered through the inner lumen 26 of the catheter body 12. In such a method the catheter body 12 can be inserted into the vasculature (for example using any technique disclosed herein) and the retrieval device advanced through the inner lumen 26 (or through another catheter, such as a microcatheter, inserted into the vasculature through the inner lumen 26) so that the device engages the thromboembolic material. The retrieval device and the material engaged thereby (together with any other catheter or microcatheter) can then be retracted into the inner lumen 26 and removed from the patient. Optionally, aspiration can be performed with or through the catheter body 12 during retraction of the retrieval device and thromboembolic material into the catheter body 12. The vasculature can comprise the neurovasculature, peripheral vasculature or cardiovasculature. The thromboembolic material may be located using any suitable technique, such as fluoroscopy, intravascular ultrasound or carotid Doppler imaging techniques.

Various examples have been described. These and other examples are within the scope of the following claims.

What is claimed is:

1. A catheter comprising:
   an inner liner defining an inner lumen;
   an outer jacket;
   a structural support member positioned between at least a portion of the inner liner and the outer jacket and defining a plurality of spaces between portions of the structural support member, wherein the structural support member comprises a first surface and a second surface separated from the first surface by a space of the plurality of spaces; and
   a support layer comprising an adhesive, the support layer mechanically connecting the structural support member to the inner liner, wherein the support layer comprising the adhesive is positioned in the plurality of spaces, and wherein the structural support member and the inner liner are not adhered to the outer jacket, and
   wherein the adhesive of the support layer is positioned in the space such that the adhesive extends from the first surface to the second surface.

2. The catheter of claim 1, wherein the structural support member comprises a coil defining a plurality of turns, the plurality of turns comprising a first turn and a second turn, and the first turn defining the first surface and the second turn defining the second surface, a first surface of the first turn of the coil and a second surface of the second turn of the coil defining the space.

3. The catheter of claim 1, wherein the structural support member comprises a braid.

4. The catheter of claim 1, wherein the support layer extends between the inner liner and the outer jacket within the plurality of spaces.

5. The catheter of claim 1, wherein the adhesive is a thermoset adhesive.

6. The catheter of claim 1, wherein only one structural support member is positioned between the outer jacket and the inner liner.

7. The catheter of claim 1, wherein the outer jacket comprises a plurality of outer jacket sections having different durometers.

8. The catheter of claim 1, wherein the outer jacket comprises a heat-shrinkable material, the outer jacket being heat shrunk over the support layer and the structural support member.

9. The catheter of claim 1, wherein no material is present between at least a portion of the structural support member and the outer jacket.

10. The catheter of claim 1, wherein the support layer is not positioned between the structural support member and the outer jacket.

11. The catheter of claim 1, wherein the inner liner, the outer jacket, and the structural support member define an elongated body, and wherein the outer jacket comprises:
a first section decreasing in durometer along a length of the first section in a direction towards a distal end of the elongated body; and
a second section more distal than the first section and including the distal end of the elongated body, the second section having a higher durometer than a distal portion of the first section, wherein the second section and the inner liner define a distal opening of the elongated body.

12. The catheter of claim 5, wherein the thermoset adhesive comprises a urethane adhesive.

13. The catheter of claim 6, wherein the inner liner, the outer jacket, and the structural support member define an elongated body, and wherein the structural support member is a single coil that progressively changes in pitch as it extends distally through the elongated body, the single coil being devoid of any joints.

14. The catheter of claim 6, wherein the inner liner, the outer jacket, and the structural support member define an elongated body, and wherein the structural support member is a single coil that progressively changes in pitch as it extends distally through the elongated body, and wherein a first pitch of the single coil in a proximal portion of the elongated body is about 0.00225 inches (about 0.057 mm), a second pitch of the single coil in a medial portion of the elongated body is about 0.00250 inches (about 0.064 mm), a third pitch of the single coil in a distal portion of the elongated body is 0.0030 inches (about 0.076 mm), and a fourth pitch of the single coil in a distal portion of the elongated body is 0.0070 inches (about 0.18 mm).

15. The catheter of claim 11, wherein the structural support member extends along the first section of the outer jacket and does not extend along the second section.

16. The catheter of claim 11, wherein a distal tip of the elongated body including the distal end of the elongated body consists essentially of the inner liner and the outer jacket.

17. The catheter of claim 11, further comprising a radiopaque marker coupled to the elongated body, wherein the elongated body distal to the radiopaque marker consists essentially of the inner liner and the outer jacket.

18. The catheter of claim 11, wherein the inner liner extends distally of a proximal end of the second section.

19. A catheter comprising:
an inner liner defining an inner lumen;
an outer jacket;
a structural support member positioned between at least a portion of the inner liner and the outer jacket and comprising a coil defining a plurality of turns, the plurality of turns comprising a first turn and a second turn; and
a support layer comprising an adhesive, wherein the support layer mechanically connects the structural support member to the inner liner and is positioned in a space defined by a first surface of the first turn of the coil and a second surface of the second turn of the coil such that the support layer comprising the adhesive extends from the first surface to the second surface, and wherein the structural support member and the inner liner are not adhered to the outer jacket.

20. The catheter of claim 19, wherein the adhesive is a thermoset adhesive.

21. The catheter of claim 19, wherein the inner liner, the outer jacket, the coil, and the support layer define an elongated body, and wherein the outer jacket comprises:
a first section decreasing in durometer along a length of the first section in a direction towards a distal end of the elongated body; and
a second section more distal than the first section and including the distal end of the elongated body, the second section having a higher durometer than a distal portion of the first section, wherein the second section and the inner liner define a distal opening of the elongated body.

22. The catheter of claim 21, wherein the structural support member extends along the first section of the outer jacket and does not extend along the second section.

23. The catheter of claim 21, further comprising a radiopaque marker coupled to the elongated body, wherein the elongated body distal to the radiopaque marker consists essentially of the inner liner and the outer jacket.

* * * * *